(12) United States Patent
Jackson et al.

(10) Patent No.: US 11,590,357 B2
(45) Date of Patent: Feb. 28, 2023

(54) OPTOGENETIC SYSTEM AND METHOD

(71) Applicant: University of Newcastle Upon Tyne, Tyne and Wear (GB)

(72) Inventors: Andrew Jackson, Tyne and Wear (GB); Mark Cunningham, Tyne and Wear (GB); Stuart Baker, Tyne and Wear (GB); Patrick Degenaar, Tyne and Wear (GB)

(73) Assignee: University of Newcastle Upon Tyne, Tyne and Wear (GB)

( * ) Notice: Subject to any disclaimer, the term of this patent is extended or adjusted under 35 U.S.C. 154(b) by 34 days.

(21) Appl. No.: 16/321,389

(22) PCT Filed: Jul. 28, 2017

(86) PCT No.: PCT/EP2017/069176
§ 371 (c)(1),
(2) Date: Jan. 28, 2019

(87) PCT Pub. No.: WO2018/020002
PCT Pub. Date: Feb. 1, 2018

(65) Prior Publication Data
US 2019/0168021 A1      Jun. 6, 2019

(30) Foreign Application Priority Data

Jul. 28, 2016 (GB) .................................... 1613033

(51) Int. Cl.
*A61N 5/06* (2006.01)
*A61B 5/00* (2006.01)
(Continued)

(52) U.S. Cl.
CPC ............ *A61N 5/0622* (2013.01); *A61B 5/291* (2021.01); *A61B 5/4094* (2013.01);
(Continued)

(58) Field of Classification Search
CPC ... A61B 5/4836; A61B 5/6868; A61B 5/0478; A61B 5/4094; A61B 5/01; A61N 5/0622; A61N 2005/0612
See application file for complete search history.

(56) References Cited

U.S. PATENT DOCUMENTS 8,583,254 B2    11/2013  Jensen et al.
2009/0088680 A1*  4/2009  Aravanis ................ A61K 38/16
                                                              604/21
(Continued)

OTHER PUBLICATIONS

Lin, J., Knutsen, P., Muller, A. et al. ReaChR: a red-shifted variant of channelrhodopsin enables deep transcranial optogenetic excitation. Nat Neurosci 16, 1499-1508 (2013). https://doi.org/10.1038/nn.3502 (Year: 2013).*
(Continued)

*Primary Examiner* — Gary Jackson
*Assistant Examiner* — Alexander M Eisenberg
(74) *Attorney, Agent, or Firm* — Kilpatrick Townsend & Stockton LLP

(57) ABSTRACT

An optogenetic system and method for preventing or halting seizures. The system and method use a sensor for monitoring the activity of a neural network containing a group of target neurons, and generating an input signal indicative of said activity, the target neurons being excitatory neurons. Excitatory stimulation is delivered in the form of an optical signal by an optical stimulator to the target neurons, the optical signal being determined based on the input signal, to reduce the overall activity of the target neurons.

28 Claims, 25 Drawing Sheets

(51) Int. Cl.
 *A61B 5/291* (2021.01)
 *A61B 5/01* (2006.01)
(52) U.S. Cl.
 CPC .......... *A61B 5/4836* (2013.01); *A61B 5/6868* (2013.01); *A61B 5/01* (2013.01); *A61N 2005/0612* (2013.01)

(56) References Cited

U.S. PATENT DOCUMENTS

| | | | |
|---|---|---|---|
| 2009/0099473 A1* | 4/2009 | Dunseath | A61B 5/6814 600/544 |
| 2011/0230936 A1* | 9/2011 | Jensen | A61N 1/36067 607/59 |
| 2012/0253261 A1* | 10/2012 | Poletto | A61N 5/0601 604/20 |
| 2012/0277619 A1* | 11/2012 | Starkebaum | A61B 5/6871 600/547 |
| 2012/0283604 A1 | 11/2012 | Mishelevich | |
| 2013/0090519 A1* | 4/2013 | Tass | A61M 21/00 600/28 |
| 2013/0190646 A1* | 7/2013 | Weinstein | A61B 5/0059 600/547 |
| 2014/0039312 A1* | 2/2014 | Rockweiller | A61B 5/1107 600/509 |
| 2014/0057232 A1* | 2/2014 | Wetmore | G09B 19/00 600/28 |
| 2016/0147964 A1* | 5/2016 | Corey | A61B 5/048 700/90 |
| 2017/0259068 A1* | 9/2017 | Tass | A61N 1/0534 |

OTHER PUBLICATIONS

Bernstein, Jacob G., and Edward S. Boyden. "Optogenetic tools for analyzing the neural circuits of behavior." Trends in cognitive sciences 15.12 (2011): 592-600. (Year: 2011).*

Breakspear et al., "A Unifying Explanation of Primary Generalized Seizures Through Nonlinear Brain Modeling and Bifurcation Analysis", Cerebral Cortex, 16, 2016, pp. 1296-1313.

Grossman et al., "Modeling Study of the Light Stimulation of a Neuron Cell With Channelrhodopsin-2 Mutants", IEEE Transactions on Biomedical Engineering, vol. 58, No. 6, Jun. 2011, pp. 1742-1751.

Krook-Magnuson et al., "On-demand optogenetic control of spontaneous seizures in temporal lobe epilepsy", Nature Communications, 4:1376, 2013, pp. 1-8.

Ladas et al., "Seizure Reduction through Interneuron-mediated Entrainment using Low Frequency Optical Stimulation", Exp Neurol. 269, Jul. 2015, pp. 120-132.

Schevon et al., "Evidence of an inhibitory restraint of seizure activing in humans", Nature Communications 3:1060, 2012, pp. 1-11.

Wang et al., "Dynamic Mechanisms of Neocortical Focal Seizure Onset", PLOS Computational Biology, vol. 10, Issue 8, e1003787, Aug. 2014, pp. 1-18.

Wendling et al., "Epileptic fast activity can be explained by a model of impaired GABAergic dendritic inhibition", European Journal of Neuroscience, vol. 15, 2002, pp. 1499-1508.

Wilson et al., "Excitatory and Inhibitory Interactions in Localized Populations of Model Neurons", Biophysical Journal, vol. 12, 1972, pp. 1-24.

Amari, "Dynamic of Pattern Formation in Lateral-inhibition Type Neural Fields", Biological Cybernetics, vol. 27, No. 2, 1977, pp. 77-87.

Cheng et al., "Optogenetic Approaches to Target Specific Neural Circuits in Post-stroke Recovery", Neurotherapeutics, vol. 13, 2016, pp. 325-340.

Chiang et al., "Seizure Suppression by High Frequency Optogenetic Stimulation Using in Vitro and in Vivo Animal Models of Epilepsy", Brain Stimulation, vol. 1, Jul. 9, 2014, pp. 890-899.

Da Silva et al., "Epilepsies as Dynamical Diseases of Brain Systems: Basic Models of the Transition Between Normal and Epileptic Activity", Epilepsia, vol. 44, 2003, pp. 72-83.

Gorski et al., "Cortical Excitatory Neurons and Glia, but Not GABAergic Neurons, are Produced in the Emx1-expressing Lineage", The Journal of Neuroscience, vol. 22, No. 15, Aug. 1, 2002, pp. 6309-6314.

Grosenick et al., "Closed-Loop and Activity-Guided Optogenetic Control", Neuron, vol. 86, Apr. 8, 2015, pp. 106-139.

Izhikevich, "Neural Excitability, Spiking and Bursting", International Journal of Bifurcation and Chaos, vol. 10, No. 6, 2000, pp. 1171-1266.

Jansen et al., "Electroencephalogram and Visual Evoked Potential Generation in a Mathematical Model of Coupled Cortical Columns", Biological Cybernetics, vol. 73, 1995, pp. 357-366.

Jirsa et al., "On the Nature of Seizure Dynamics", Brain, A Journal of Neurology, vol. 137, 2014, pp. 2210-2230.

Newman et al., "Optogenetic Feedback Control of Neural Activity", eLife, vol. 4, Jul. 3, 2015, 24 pages.

Paz et al., "Closed-loop Optogenetic Control of Thalamus as a Tool for Interrupting Seizures After Cortical Injury", Nature Neuroscience, vol. 1, No. 1, Jan. 2013, pp. 64-70.

Taylor et al., "A Computational Study of Stimulus Driven Epileptic Seizure Abatement", PLoS One, Dec. 22, 2014, 26 pages.

Tonnesen et al., "Optogenetic Control of Epileptiform Activity", PNAS, vol. 106, No. 29, Jul. 21, 2009, pp. 12162-12167.

Wang et al., "Phase Space Approach for Modeling of Epileptic Dynamics", Physical Review, vol. 85, 2012, pp. 061918-1-061918-11.

Weiss et al., "Ictal High Frequency Oscillations Distinguish Two Types of Seizure Territories in Humans", Brain, A Journal of Neurology, vol. 136, 2013, pp. 3796-3808.

Witt et al., "Controlling the Oscillation Phase through Precisely Timed Closed-loop Optogenetic Stimulation: A Computational Study", Frontiers in Neural Circuits, vol. 7, Article 49, Apr. 17, 2013, pp. 1-17.

Wykes et al., "Optogenetic and Potassium Channel Gene Therapy in a Rodent Model of Focal Neocortical Epilepsy", Epilepsy, vol. 4, Issue 161, Nov. 21, 2012, pp. 1-10.

* cited by examiner

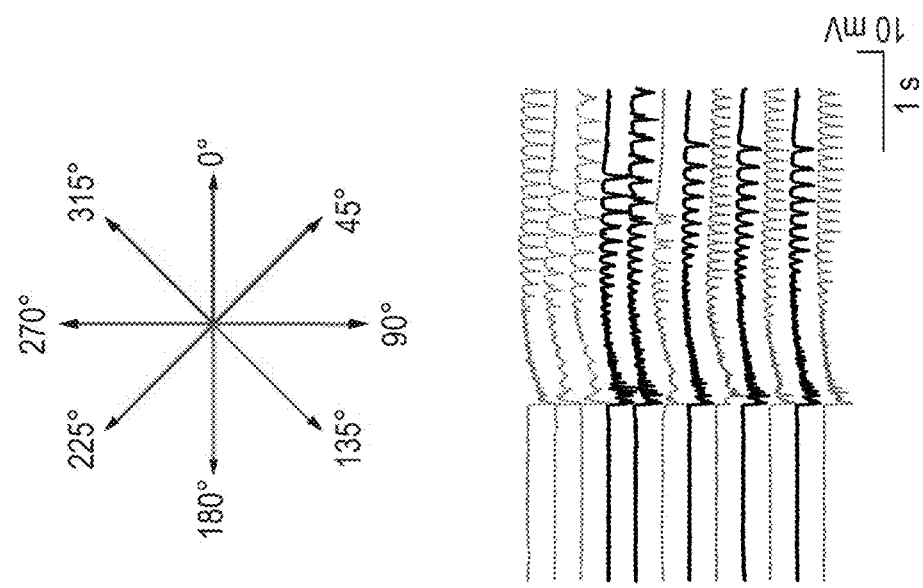
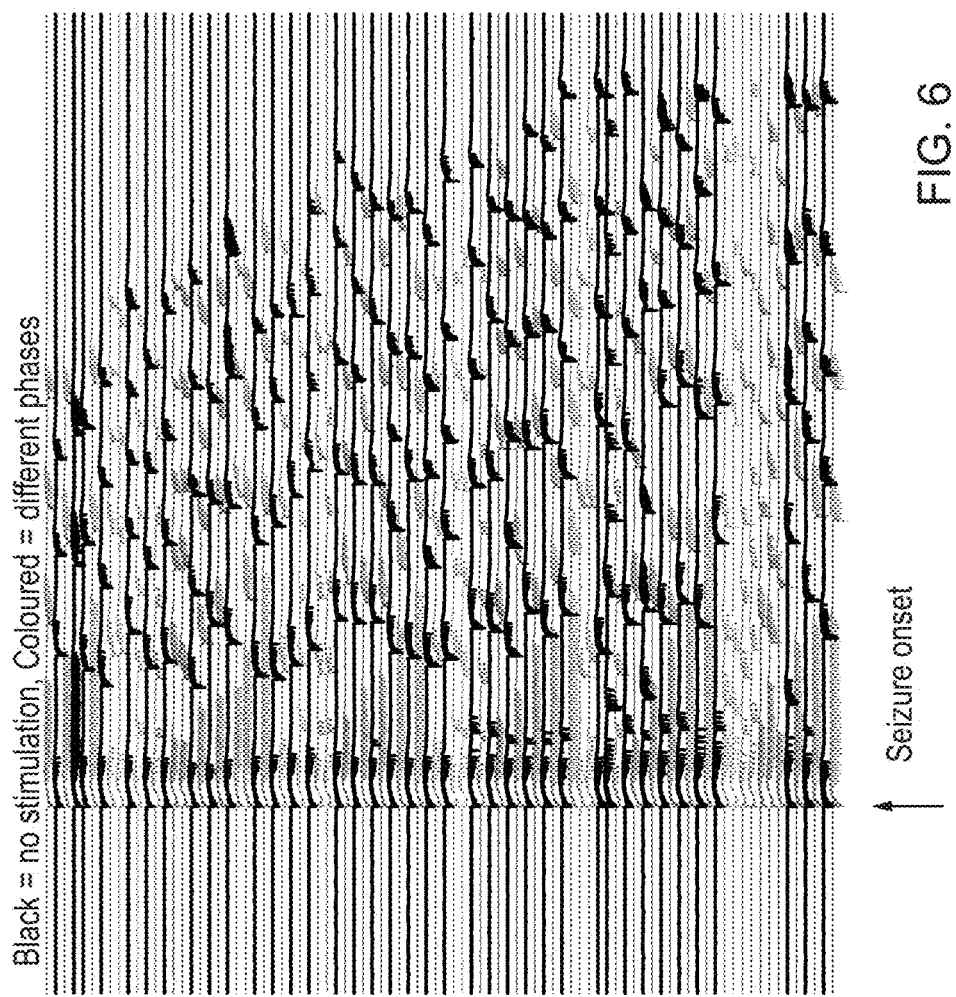
FIG. 6

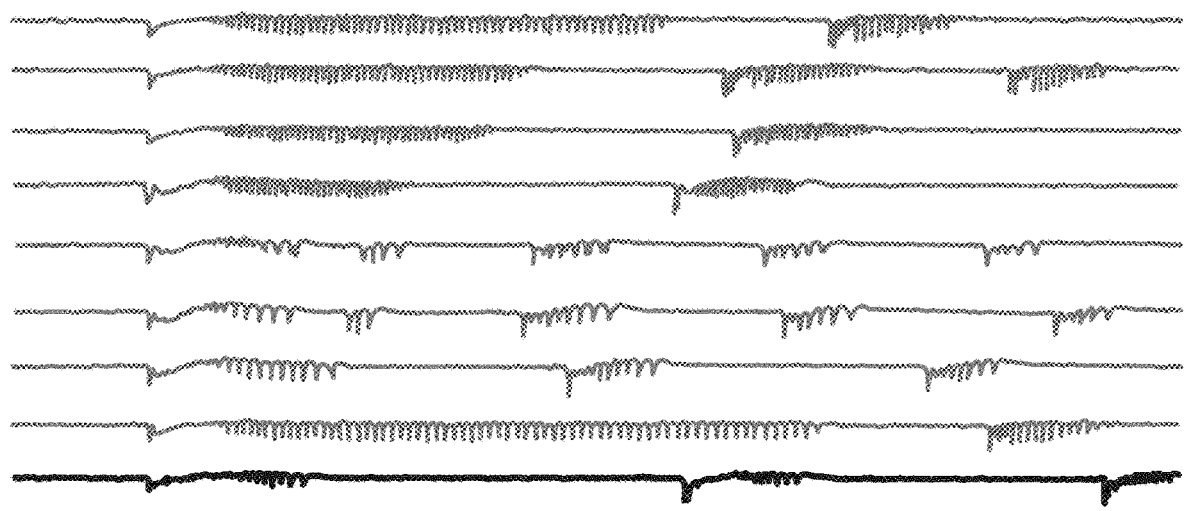
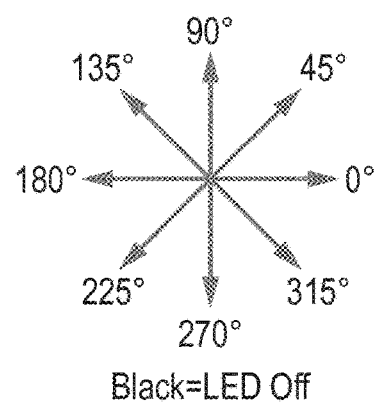
Black=LED Off
FIG. 14

OPTOGENETIC SYSTEM AND METHOD

The present application is a U.S. National Stage Application of PCT/EP2017/069176 filed Jul. 28, 2017; which claims priority to GB Application No. 1613033.8 filed Jul. 28, 2016.

FIELD OF THE INVENTION

The present invention relates to an optogenetic system for the halting or prevention of seizures, a control device for use in such a system, and a method of halting or preventing seizures.

BACKGROUND OF THE INVENTION

The brain is made up of around 100 billion neurons, which are responsible for transmitting signals throughout the body, in the form of propagating electrical pulses. These pulses propagate in the form of an action potential. Action potentials arise when a threshold potential difference is applied across the neuron membrane (also referred to as a membrane potential), and are seen as a spike in the potential difference across the membrane, i.e. a rapid depolarization. Prolonged stimuli, rather than affecting the amplitude or duration of an action potential, instead result in a series of identical action potentials, the frequency of which depends on the intensity of the stimulus. When an action potential is generated in a neuron, this may be referred to as "firing".

Fundamental to the transmission of signals from one part of the body to another is the ability of signals to pass from one neuron to another. The region where two different neurons meet is known as the synapse, and the neurons either side of the synapse may be referred to as pre-synaptic neurons and post-synaptic neurons. A given post-synaptic neuron may be contacted by several pre-synaptic neurons. Rather than propagating in the form of electrical pulses, signals are chemically transmitted across a synapse, by neurotransmitters. More specifically, when an action potential arrives at the synapse, a neurotransmitter is released, which travels across the synapse to the post-synaptic neuron. Broadly speaking, there are two types of neurotransmitter, which are referred to herein as excitatory and inhibitory neurotransmitters:

Excitatory neurotransmitters induce a change in the post-synaptic neuron which causes the potential difference across the membrane to approach the threshold level. The most common excitatory neurotransmitter is glutamate. Neurons which release excitatory neurotransmitters are known as excitatory neurons or excitatory cells.

Inhibitory neurotransmitters induce a change in the post-synaptic neuron which causes the potential difference across the membrane to move away from the threshold level. The most common inhibitory neurotransmitter is GABA. Neurons which release inhibitory neurotransmitters are known as inhibitory neurons or inhibitory cells.

A single action potential is usually insufficient to trigger an action potential in the post-synaptic neuron. However, multiple action potentials (either from the same pre-synaptic neuron or several different pre-synaptic neurons) can sum to cause an action potential to be triggered in the post-synaptic neuron. As mentioned above, several (occasionally up to 10,000) pre-synaptic neurons may be connected to a given post-synaptic neuron, and these may be made up of a combination of excitatory and inhibitory neurons. The effect of the excitatory and inhibitory neurons is summed over time, with the action potential only being triggered in the post-synaptic neuron when the temporal sum of the effects of the inhibitory and excitatory neurons reaches the threshold value. In this way, inhibitory neurons regulate the ability of an excitatory neuron to stimulate a response in a post-synaptic neuron.

The susceptibility of an action potential to be triggered in a given post-synaptic neuron is referred to as the excitability. Seizures can result from hyperexcitability, which can result from, amongst other things, increased excitatory synaptic neurotransmission or decreased inhibitory neurotransmission.

Epilepsy is a chronic disorder of the brain, characterized by a heightened susceptibility to seizures, which affects an estimated 65 million people worldwide, and may be characterized by excessive firing of neurons in the brain. About 30% of cases of epilepsy are refractory to anti-epileptic medications. These patients with so-called "refractory epilepsy" can potentially be treated surgically, either by surgical resection or (electric or magnetic) brain stimulation. However, the likelihood of success resulting from these treatments is relatively small and up to 30% of treated subjects continue to suffer from seizures. Recently, the development of optogenetic technology has enabled an alternative strategy for treating epilepsy. Unlike resective surgery, optogenetic therapies are adaptable and reversible, and offer more finesse than electric brain stimulation.

Specifically, optogenetic treatments use light to control cells in living tissues which have been genetically modified to respond to light incident upon them. Optogenetics usually involves the use of gene therapy to promote the expression of genes which encode for the production of optogenetic actuators, such as opsins. In the treatment of neurological conditions such as epilepsy, neurons are modified to create receptors or ion channels which are light-sensitive. Ion channels can be expressed on inhibitory neurons, which cause e.g. increased GABA activity upon activation, thus increasing the inhibitory behaviour of these cells, and suppressing action potentials on post-synaptic neurons. This technique is demonstrated for temporal lobe epilepsy in mice in Krook-Magnuson et al. (Krook-Magnuson, E., Armstrong, C., Oijala, M. & Soltesz, I. On-demand optogenetic control of spontaneous seizures in temporal lobe epilepsy. *Nature communications* 4:1376 (2013)) where, upon detection of a seizure, optogenetic stimulation is used either to inhibit the action of principal (i.e. excitatory) cells, or to activate a population of GABAergic (i.e. inhibitory) cells, in order to halt a seizure in a few seconds.

The approach proposed in the Krook-Magnuson paper is not without its problems. For example, when exciting the inhibitory cells, the opsins must be selectively expressed only in the inhibitory cells. In humans, this can only be achieved by promoter-driven expression. This generally leads to low expression levels, and accordingly and thus potentially an inefficient control of the network.

Inhibitory opsins tend to be expressed in the forms of ion pumps, rather than ion channels, which are less efficient, and leads to problems when taking the approach of inhibiting the excitatory cells.

SUMMARY OF THE INVENTION

As discussed above in the previous section, conventional optogenetic techniques and systems which are used in the treatment of seizures, epileptic or otherwise, rely on applying an excitatory stimulus to inhibitory (e.g. GABAergic)

neurons, or applying an inhibitory stimulus to excitatory (e.g. glutamatergic) neurons. Herein, the term "excitatory stimulus" is used to refer to a stimulus which acts to depolarize the neuron, e.g. an influx of $Na^+$ or $Mg^{2+}$ ions, to bring the membrane potential closer to the threshold, i.e. a stimulus which encourages the firing of neurons. "Inhibitory stimulus" is used to refer to a stimulus which acts to hyperpolarize the neuron, e.g. an influx of $Cl^-$ ions, causing the membrane potential to move away from the threshold, thus inhibiting the neuron from firing. Broadly speaking, aspects of the present invention are directed towards a counter-intuitive technique in which an excitatory stimulus is applied to a population of excitatory neurons in such a manner that allows the prevention of seizures before they occur, or that is able to halt a seizure which has already begun.

A key advantage of the use of optogenetic techniques rather than e.g. electronic techniques such as electrode-based deep brain stimulation is that measurements may be taken at the same time as the stimulation is being delivered. In "electronic only" systems, the application of electronic stimuli cannot be performed at the same time as measurement using the same electrodes, due to the disruption caused. This prevents continuous closed-loop feedback operation, which as is described in detail below, is an important advantage of the present invention.

Accordingly, a first aspect of the present invention provides an optogenetic system for preventing or halting seizures, the system including:

a sensor for monitoring the activity of a neural network containing a group of target neurons, and generating an input signal indicative of said activity, the target neurons being excitatory neurons;

an optical stimulator for delivering an excitatory stimulus in the form of an optical signal to the target neurons, the optical signal determined based on the input signal, to reduce the overall activity of the target neurons.

Herein, "prevention" or "preventing" of seizures refers to cases in which the seizure does not begin at all, i.e. the patient does not have a seizure. "Halting" refers to cases in which the seizure does begin, but is swiftly stopped due to the operation of the optogenetic system as claimed. The advantages of this invention, and the mechanism by which it is able to achieve these advantages, are best understood from a consideration of the "state space" representation of the brain. This is explained in detail with reference to FIGS. 3A and 3B in the "Detailed Description" section of this application.

In the present application, the term "excitatory neuron" refers to a neuron which releases primarily excitatory neurotransmitters, i.e. those which act to stimulate an action potential in other (post-synaptic) neurons. Examples of excitatory neurons which may form the target neurons of the present invention are glutamatergic neurons. Here, and throughout the application, reducing the "overall activity of the target neurons" (or similar) generally refers to a decrease in the level of activity which is monitored by the sensor. For example, this decrease in activity may refer to a decrease in the number of action potentials discharged by the target neurons. The activity may be associated with seizures or seizure-like events (SLEs), and thus a reduction in the overall activity may advantageously lead to the prevention or halting of seizures or SLEs.

The target neurons are preferably genetically modified to respond to optical stimuli. The target neurons are excitatory neurons, and they are preferably genetically modified to execute excitatory behaviour in response to an optical stimulus. The target neurons may be modified by using a virus to infect the cells with the opsin DNA. The virus may be injected into the brain and infects neurons in the vicinity. Expression is preferably restricted to only the excitatory cells. Though in other embodiments both excitatory and inhibitory neurons may express the (excitatory) opsin. "Excitatory behaviour" refers to behaviour which stimulates an action potential in the neurons expressing the opsin, such as the opening of ion channels which allow the influx of positively-charged ions such as $Na^+$, $Mg^{2+}$, and $Ca^{2+}$ to effect depolarization (mainly at the cell body of the neuron), and thus the probability of the target neurons firing action potentials ("Excitatory behaviour" should not be confused with the behaviour of excitatory neurons, which are those neurons which excite post-synaptic neurons). This may be achieved through genetic modification of the target neurons to express optogenetic actuators such as opsins, which are light-sensitive proteins. Preferably the target neurons are modified so that when an optical stimulus is applied to the opsin, the opening of positive ion-channels is caused or any other cellular activity which may stimulate an action potential. In preferred embodiments, the target neurons are genetically modified to express opsins such as Channelrhodopsin 2 (ChR2), Chronos, Chrimson, and ReaChR.

The optogenetic system may include an implantable device on which the sensor is located, or mounted. In this, the monitoring or measurement by the sensor is more accurate since there may be less tissue between the sensor and the brain tissue of interest, i.e. that tissue containing the neural network which contains the target neurons. The sensor of the present invention is preferably configured to measure the electrical activity of the neural network containing the target neurons, and accordingly therefore includes an electrode. Accordingly, the input signal is preferably an electrical signal. There are numerous bioelectric signals which may be detected, but the sensor is preferably configured to monitor the local field potential, which is a signal obtained by measuring the extracellular potential (voltage) in the brain tissue containing the neural network containing the target neurons. The LFP represents a mixture of the activity of the inhibitory neurons and the excitatory neurons. An LFP which is measured as described provides results which are similar to an EEG but with more spatial accuracy, and similar to an EEG, the LFP varies as a result of synaptic activity.

In order to measure electrical activity across a neural network, the sensor preferably includes a plurality or array of electrodes distributed over the volume occupied by that neural network. To ensure that results are taken from the whole of the neural network of interest, the array of electrodes are preferably evenly spatially distributed.

The implantable device on which the sensor is located or mounted may include a shaft, implantable into the brain tissue of a patient, at least one electrode being located on the shaft, and preferably a plurality of electrodes. In embodiments where there are a plurality of electrodes on the shaft, they are preferably evenly-spaced relative to each other. The implantable device may include a plurality of shafts, which may be identical or substantially identical to each other, at least one electrode located on each shaft. These shafts may be arranged in a one-dimensional or two-dimensional array. In this way, it is possible that the plurality of electrodes are arranged in a manner whereby they can monitor a three-dimensional volume of brain tissue. The shafts are preferably made of a biocompatible material. Each shaft may also include an electronics module such as a CMOS module configured to receive signals from each of the electrodes on the shaft on which that electronics module is located. The electronics module may output the signals received from the electrodes to a processor.

Alternatively, the electrodes may be connected directly to a processor, i.e. not via a separate electronics module.

In order to ensure that there is a fixed distance between the shafts, the sensor preferably also includes a structure configured to maintain even spacing between the shafts. For example, the structure may be in the form of a board containing apertures, each aperture arranged to receive one of the shafts, and the apertures arranged in a regular one-dimensional or two-dimensional array.

Alternatively, rather than an implantable electrode array, an EEG-like arrangement may be employed, in which the electrode or electrodes are to be located on the patient's scalp. Additionally, the sensor may also include a temperature sensing element, to monitor the temperature of the brain tissue containing the neural network containing the target neurons. In this way, the optogenetic system is able to detect when the temperature of the brain tissue is too high, and accordingly prompt the optical stimulators to stop providing the excitatory stimulus, for safety purposes.

The optical stimulator of the present invention may also be located or mounted on an implantable device, which in preferred embodiments is the same as the implantable device on which the sensor is located or mounted. In order to provide ample stimulation to the target neurons, e.g. to excite the opsin which has been expressed in the excitatory neurons, the optical stimulator preferably includes a light-emitting element configured to deliver ultra-high intensity light, the light preferably having an intensity of no less than $0.5$ mW/mm$^2$ and more preferably no less than $1$ mW/mm$^2$. In order to deliver this light directly to the target neurons or the neural network including those target neurons, the optical stimulator is preferably implantable. Accordingly, the optical stimulator may include a light-emitting element such as a light-emitting diode or a laser. In order to minimize the size of the implanted portion of the optical stimulator or indeed the whole optogenetic system, and therefore the invasiveness experienced when it is in place, the LED is preferably a micro-LED. Rather than a single, larger light-emitting element, the optical stimulator of the optogenetic system preferably includes an array or plurality of light-emitting elements. Like the electrodes, these may be arranged on a shaft or plurality of shafts, with one or more light-emitting elements on each shaft.

The implantable device on which the optical stimulator is preferably located or mounted may comprise a plurality of shafts, arranged in an array. As discussed above, each shaft may include at least one electrode and/or at least one light-emitting element. Preferably, each shaft includes at least one electrode and at least one light-emitting element, and more preferably each shaft includes a plurality of each. Preferably the implant includes a structure as discussed with reference to the electrode shafts, which is configured to maintain even spacing between the shafts, for example a board containing a plurality of apertures, each configured to receive a shaft. By having the electrodes and light-emitting elements on the same shaft, this allows the plurality of each to be more evenly distributed while maintaining a relatively compact arrangement. Furthermore, since it is preferable for the light-emitting elements to be implanted into the brain tissue, it is also more convenient to monitor the activity of the brain tissue using the same implant. The shafts having LEDs and electrodes disposed thereon may be referred to herein as optrodes, the optrode array, or optrode shafts.

The implantable device (having an optrode array located thereon), may be connected to a separate base station which is configured to be located outside the skull. The connection may be via a first type of cable, such as a flexible ribbon cable. A flexible cable is preferable in order to accommodate for relative movement between the brain and the skull. In embodiments in which the processor is located on a chest unit, the base station may be connected to the chest unit via a second type of cable, which is less flexible, i.e. sturdier than the first type of cable. By having the processor, or chest unit connected to the implantable device via a base station, from which the processor or chest unit is separable, it is possible to remove/replace the processor or chest unit without having to remove the implantable device from the user's brain, for example in case of infection.

In some embodiments, there may be plurality of arrays or electrodes and/or optical stimulators distributed throughout the brain, in order to combat multiple foci seizures. Specifically, the optogenetic system may include a plurality of implantable devices, as described above, to provide a plurality of optrode arrays. In preferred embodiments, more than one of the implantable devices may be connected to the same base station. Even more preferably still, all of the implantable devices may be connected to a single base station, as described above.

Then, the shafts may be arranged in a one-dimensional or two-dimensional array, to provide a three-dimensional array of light-emitting elements. Instead of LEDs, the light-emitting elements may also include any of the following: a laser such as a vertical cavity surface emitting laser, a Bragg laser, or other lasing structure. The preferred wavelength of the optical signal forming the excitatory stimulus depends on the opsin which is expressed by the target neurons. For example: 470 nm light is preferable for ChR, and 590-630 nm light is preferable for redshifted opsins such as ReaChR.

As will be explained in detail later on in the application, it may be seen that it in the present invention, both the amplitude and the phase of the optical signal contribute to the reduction in the overall activity of the target neurons, and accordingly the halting or prevention of seizures or seizure-like events. In the neural network of interest in the present invention, there is a population of inhibitory neurons and a population of excitatory neurons, each population having an associated activity. During a seizure, these activities fluctuate rapidly, and accordingly the activity of each of the populations may be represented by a high-amplitude, high-frequency oscillatory signal, these signals having the same, or approximately the same frequency. Generally this frequency is around 1 to 20 Hz, depending on the individual. The input signal is representative of these signals. In some embodiments, the input signal may be representative of one or other of these activities, and in other embodiments, the input signal may be representative of a combination of the two. Either way, the input signal generally has the same frequency as the oscillatory signals which are representative of the activities of the target neurons. In order to determine or generate the optical signal, the optogenetic device may include a processor which is configured to perform processing steps on the input signal, to generate an output signal based on the input signal, the output signal being used to generate the optical signal which forms the excitatory stimulus. Specifically, the processing steps which are performed on the input signal are preferably performed in the electrical domain, for example computationally. The output signal is accordingly preferably an electrical signal. This output signal is then supplied to the optical stimulator, or plurality of optical stimulators, in order to generate the optical signal which is applied to the target neurons. Thus, either the sensor or the optical stimulator may include a modulator configured to generate an optical signal from the electrical output signal. Alternatively, the modulator may form part of the processor, or a separate part of the optogenetic system entirely.

The processor may be connected to the sensor and/or optical stimulator via connective leads. Specifically, the processor may be located in a separate module, which is configured to be secured to a separate part of a user's body. For example, the processor may be located in a chest unit.

In addition to the monitoring of the activity of the neural network, the sensor and/or processor may also be configured to detect (or identify) the oscillatory signals, described above, which are indicative of the onset or presence of seizures or seizure-like events. Here, it is worth noting that "onset" refers to signals that a seizure is about to being, and "presence" refers to seizures which are already in progress. These signals may be referred to as event signals. Specifically, the processor is preferably configured to detect event signals within the input signal it receives from the sensor. Alternatively, however, the sensor itself may be configured to detect the event signals, and to send to the processor the input signal, and information about the event signals, for subsequent processing.

Subsequent processing steps preferably only occur in response to the detection of event signals. In particular, it is preferred that the excitatory stimulus is only applied to the target neurons in response to the detection of event signals, indicative of a seizure or seizure-like activity. For example, the processor may be configured only to generate an output signal upon detection of an event signal. In this way, external interference with the activity of the target neurons may be kept to a minimum. When the excitatory stimulus is delivered only in response to an event signal, indicating that a seizure is about to begin, it is possible to prevent the seizure from occurring altogether, which is clearly advantageous. Alternatively, when the excitatory stimulus is delivered in response to an event signal indicating the occurrence of a signal, the seizure may be halted within a few seconds. The same applies for seizure-like events. The effect of the excitatory stimulus (i.e. the optical signal) is to halt or prevent a seizure. Accordingly, the activity of the target neurons changes to reflect this. As a result in the change of the activity, the output signal of the processor also changes, thus changing the output of the optical stimulator. Since the output of the optical stimulator directly affects the measurement which controls the output of the optical stimulator in the first place, the system executes closed-loop feedback control, and the processor may therefore be a closed-loop control device The determination of the form of the output signal used to generate the optical signal is best understood from a consideration of the state space representation of the brain. In this, a given "state" is represented by a plot of the activity of the inhibitory population, against the activity of the excitatory population. This is explained in detail with respect to FIGS. 3A and 3B, later in the application. During the cycles of oscillatory activity, there are given times at which excitatory stimulation acts to move the brain state towards, or into the stable region, and it is at these times when it is preferable to apply the maximum excitatory stimulus. These times are present in each of the oscillatory cycles of the activity of the excitatory or inhibitory neurons, and as such the input signal is also oscillatory in nature, and it is preferable that the optical signal has the same frequency as the input signal, and may also be an oscillatory signal.

The times at which it is most desirable to provide the maximum excitatory stimulus do not generally coincide with the peak activities of the excitatory population or the inhibitory population. Accordingly, the output signal which is used to generate the optical signal is preferably phase-shifted relative to the input signal, and thus the processor is further configured to determine or calculate the phase shift.

The phase-shift may be predetermined, and may have a fixed value. For example, the output signal has a phase shift of approximately 90° relative to a signal representing the activity of the excitatory population of neurons, i.e. the target neurons.

However, as mentioned above, in some embodiments the sensor is configured to measure the local field potential (because this is more straightforward than measuring the activity only of the target neurons), to give a value representative of a combination of the activities of the inhibitory and excitatory populations. In other words, it is preferable that the input signal is representative of the LFP.

Because the LFP contains information relating to two oscillating signals which are not in phase with each other, it is generally not in phase with (but with the same frequency as) both the activity of the inhibitory and excitatory populations. Specifically, the activity of the excitatory cells is most likely to be associated with either a negative LFP or a positive LFP, and accordingly, in order to deliver the excitatory stimulus when the cells are least active, the phase shift can be between (and including) −30° and +30°, or between 150° and 210°. The phase shift may be between (and including) −20° and +20°, or between 160° and 200°. The phase shift may be between (and including) −10° and +10°, or between 170° and 190°.

In other embodiments, the phase shift may be constant or substantially constant, and chosen to match that which has been shown to be successful in previous experimental tests, which are discussed in detail with reference in particular to FIGS. 6, 9A and 9B later on in the application. For example, the phase shift may be between no less than 60°, no less than 70°, no less than 80°, or no less than 90°. Similarly, the phase shift may be no more than 165°, no more than 155°, no more than 145°, or no more than 135°. Alternatively, and in preferred embodiments, the phase shift may be determined based on the input signal, in order to be appropriate for a specific user. Specifically, the processor may be configured to identify the stages at which the application of the excitatory stimulus is likely to have the greatest effect in terms of causing the brain state to approach or enter the stable region. In other words, the processor may be configured to identify a range of phases during an oscillation of the input signal at which the delivery of the excitatory stimulus causes the brain state to approach the stable region, and to calculate the phase shift based on this identification. For example, in one embodiment the identification (as described above) may take into account the high-frequency components of the input signal (i.e. the local field potential) since these components reflect neural activity more directly, in order to determine which LFP phase is associated with the neural activity. Then the processor is configured to generate an output signal which is opposite in phase to this signal, or substantially opposite in phase.

In another embodiment, the LFP response to open-loop stimulation could be used to calibrate the phase-shift. Specifically, the optical stimulator could be configured to deliver a test signal (preferably a sinusoidal, or substantially sinusoidal signal) at the same frequency as an event signal, and then the sensor is configured to monitor the resultant local field potential in the form of the input signal. The output signal may then be phase-shifted, relative to the input signal, the phase shift being opposite to the phase shift between the test signal and the resultant input signal. For example, if the resultant input signal is in-phase with the test signal, then the output signal should be 180° out of phase with the input signal. After the test signal is delivered, and the phase shift determined, this phase shift is maintained, i.e. a closed-loop algorithm is then applied, which no longer involves applying a test signal continuously.

It should be noted that in the embodiments described above there is a one-off determination of the phase shift which should be used, but the output signal is continuously determined, by applying this phase shift to the input signal (and optional subsequent processing described below). In other words, it is preferable that the phase shift is constant or fixed.

Similarly, in another embodiment, a plurality of phase shifted test signals may be delivered to the target neurons, and the phase-shift which produces the greatest reduction in seizure like activity may be selected for the closed-loop algorithm.

In some embodiments, the output signal (and accordingly the optical signal) may simply be an oscillatory signal having the same form as the input signal, with a phase shift relative to the input signal. However, in other embodiments, determination of the output signal may include further processing steps. For example, it is desirable only to stimulate the target neurons in response to the activity which is indicative of seizures or seizure-like events. As has been discussed above, this activity generally has a high-frequency of around 1 to 20 Hz. So, in preferred embodiments of the present invention, the processor is configured to perform band pass filtering on the input signal, the band-pass filtering having a predetermined filter frequency. This filter frequency is the frequency around which the band-pass filtering is centred. Band-pass filtering removes any components of the input signal which have a frequency falling outside a desired range, the ranged defined by the filter frequency. The filter frequency is preferably no less than 1 Hz and/or no more than 20 Hz, to reflect the frequencies of event signals which are indicative of seizures or seizure-like activity. The phase shift is preferably applied to the output signal after the band-pass filtering, but the phase shift may also be applied before the band-pass filtering.

In addition to phase-shifting and band-pass filtering, the processor may also be configured to perform a thresholding/rectification step on the input signal. This step is preferably performed after the band-pass filtering step. Specifically, the processor may be configured to apply a threshold to the input signal, and then to rectify the signal (i.e. apply a modulus function to ensure that all parts of the signal are positive, as must be the case when converting the output signal to an optical signal). By applying a threshold in this way, it is possible to ensure that the amplitude of the output signal is proportional to the extent to which the input signal exceeds a defined threshold.

In the embodiments discussed above, a time-shift or time-delay may be used instead of a phase shift. Calculation of the time-delay may be performed in substantially the same way as the calculation of the phase-shift. The optional features set out in this application in relation to the phase-shift apply equivalently to the time-delay, where compatible.

Once the processor has performed any or all of the steps outlined in the preceding paragraphs, as discussed, the output signal is used to generate the optical signal which forms the excitatory stimulus. The output signal is preferably used to control the intensity of the light emitted by e.g. the light-emitting element of the optical stimulator in order to generate the optical signal which forms the excitatory stimulus (e.g. using a simple electrical-to-optical converter). In alternative embodiments, the output signal may be used to modulate the width or frequency of pulses of light of a constant intensity in order to generate the optical signal which forms the excitatory stimulus. The optical stimulator or the processor may include a modulator to control this.

A key advantage of this invention comes from the ability of the system to monitor the activity of the target neurons and then to optically stimulate these neurons based on that monitoring, i.e. in a closed-loop feedback system. In some embodiments, as set out above, this feedback is provided by a control device. Accordingly, a second aspect of the present invention provides a control device for use in an optogenetic system for preventing or halting seizures having:

an input for receiving an input signal indicative of the activity of a group of target neurons, the target neurons being excitatory neurons;

a processor for determining an output signal based on the input signal; and an output for transmitting the output signal to an optical stimulator;

wherein:

the output signal is determined such that when the optical signal is delivered to the target neurons, the overall activity of the target neurons is reduced.

The determination of the output signal performed by the processor of the second aspect of the invention may employ the same techniques as in the first aspect of the invention. For example, the signal may have a fixed phase relation, relating to the input signal, in order to ensure that the overall activity of the target neurons is reduced, thus then being able to halt or prevent seizures.

A further aspect of the invention, which may be performed using the system of the first aspect of the invention, or a system including the control device of the second aspect of the invention, or otherwise, provides a method of halting or preventing seizures, the method involving the steps of:

monitoring the activity of a group of target neurons in a patient, the target neurons being excitatory neurons;

generating an input signal indicative of the activity of the target neurons;

determining, based on the input signal, an optical signal for stimulating the target neurons, such that when delivered to the target neurons, the overall activity of the target neurons is reduced; and delivering an excitatory stimulus to the target neurons, in the form of the determined optical signal.

The optional method steps which embodiments of the first aspect of the invention are configured to perform may also be applied in combination with the method of the third aspect of the present invention.

Further optional features of the invention are set out below.

BRIEF DESCRIPTION OF THE DRAWINGS

Embodiments of the invention will now be described by way of example with reference to the accompanying drawings in which:

FIG. 6 shows a series of plots of the activity of target neurons, when stimulated at different phase shifts by the optical stimulator.

FIG. 14 shows an expanded plot for optogenetic modulation of SLE durations by closed-loop optogenetic stimulation in neocortical slices of EMX-ChR2 mice (Colour code for different phase-shifts is inset).

DETAILED DESCRIPTION

Figure 1:
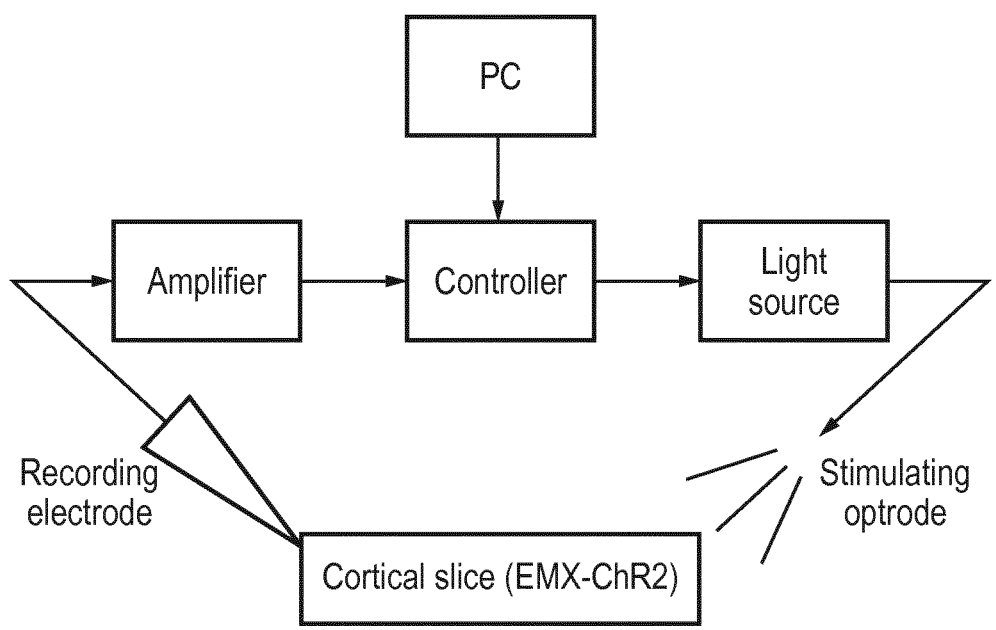
FIG. 1 shows a schematic diagram of an optogenetic system as provided by the present invention.

FIG. 1 shows a schematic diagram of an optogenetic system according to the present invention. The system illustrated, and which is described below, was used in experiments to test the effectiveness of systems and methods of the present invention in mice. In the system shown, experiments were carried out on a cortical slice from an EMX-ChR2 mouse, having a thickness of 400 μm, shown schematically at the bottom of FIG. 1. ChR2 is selectively expressed in excitatory pyramidal neurons using an EMX promoter. A recording electrode is implanted into the cortical slice, in order to monitor the activity (in this case, the local field potential) of cells within the slice, which includes contributions from excitatory neurons (e.g. glutamatergic cells) and inhibitory neurons. In the experimental setup, the recording electrode is in the form of a multi-electrode array (MEA). Signals recorded by the MEA are then transferred to an amplifier, from which they are transferred to a controller in the form of an input signal. A closed-loop algorithm as described in the previous section is then applied to the input signal in the controller to generate an output signal, the closed-loop algorithm controlled by the PC connected to the controller. The output signal is then sent to the light source whereupon it is converted into an optical signal. In this embodiment, the optical signal (i.e. the excitatory stimulus) is delivered via a 200 μm patch cord, to a 473 nm LED cube, the intensity modulation of the light controlled by the controller. In order to induce seizure-like activity in the cortical slice, 4-aminopyridine (4AP) is applied.

Figure 2:
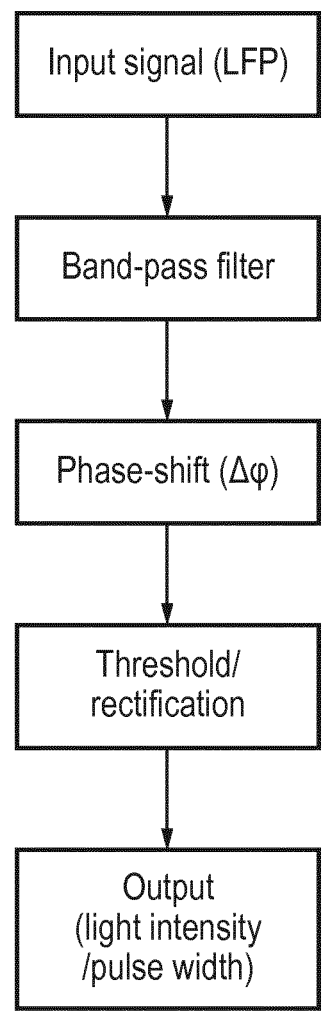
FIG. 2 shows a flowchart of the steps performed by the controller shown in FIG. 1.

FIG. 2 shows a flow chart of the method performed by the controller (or processor) shown in FIG. 1. The input signal such as an LFP is received from the sensor (i.e. the recording electrode), at the controller, whereupon it is band-pass filtered, as described earlier in the application. The seizure frequency is generally 1-20 Hz, but this may vary from patient-to-patient. After band-pass filtering, the signal is phase shifted by $\Delta\phi$ as discussed below. Then, thresholding and rectification is performed to give an output signal, which is then used to modulate the intensity or pulse width/frequency of light delivered by the stimulating optrode as shown in FIG. 1, to give a stimulation having a form similar to that shown in FIG. 4A or 4B.

Figure 3A:
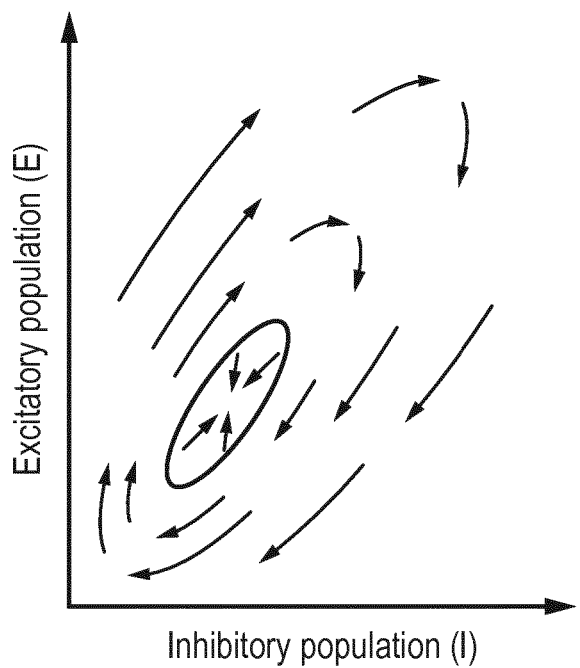
FIGS. 3A and 3B show state space representations of the brain.

FIG. 3A shows a schematic state space representation of brain activity in a recorded area. Specifically, we take a neural population view/model, where a population of excitatory neurons, and a population of inhibitory neurons interact with each other. The activities of these populations are not fixed: rather, they are dynamic, and evolve continuously with time, and the instantaneous brain state is determined by the instantaneous activities of the excitatory population and the inhibitory population. This is shown in FIG. 3A, in which the activity of the inhibitory population (I) is plotted on the x-axis, against the activity of the excitatory population (E) on the y-axis. A given location on the graph represents an individual state, which in this simplified model, is determined by only the values of E and I. The arrows represent the evolution of the system, i.e. as it evolves from one state to another state. The central shaded region represents the set of stable states. In these regions, there is little to no fluctuation in the activities of the inhibitory and excitatory populations. This principle can be applied to background and seizure states.

The state space representation of the brain is also useful for understanding what happens during a seizure. This is shown by the non-shaded region with the larger arrows, in FIG. 3A. During a seizure or seizure-like event, the brain state rapidly changes, moving elliptically as shown in FIG. 3A. This represents a relatively high-frequency, (usually around 1 to 20 Hz) fluctuation in the activities of the inhibitory and excitatory populations. Large excitatory activity excites the inhibitory population, which then in turn inhibits the excitatory population. The decrease in the activity of the excitatory population then reduces the excitation of the inhibitory population, causing the activity of the excitatory population to rise again. This process repeats itself to give the elliptical cycles shown in FIG. 3A.

Figure 3B:
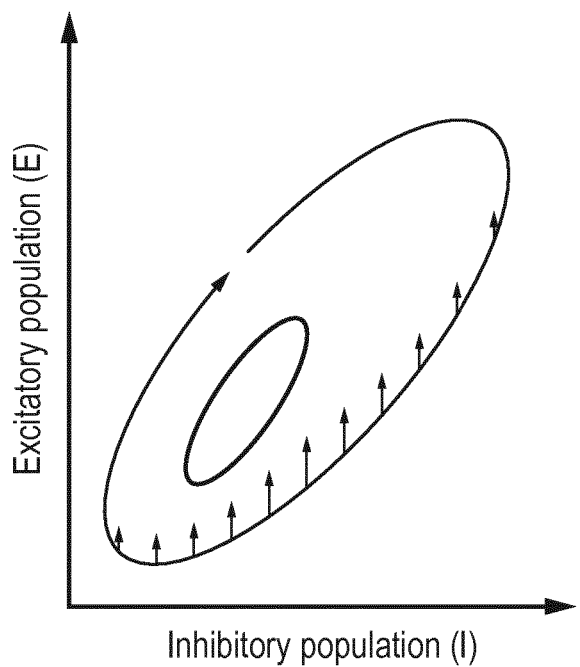

In the present invention, unlike known techniques, the seizures or SLEs are halted or prevented by the application of an excitatory optical stimulus to excitatory neurons. This may seem counter-intuitive, but the mechanism behind such a technique may be best understood with reference to FIG. 3B. In this plot, the ellipse represents the evolution of the brain state, and demonstrates its cyclical nature. By applying an excitatory stimulus, in this case optogenetically, the population of excitatory neurons in the neural network of interest (i.e. that which is monitored by the sensor) is increased. The effect of this increase in population is for the state to move to a vertically higher position on the plot shown in FIG. 3B. This is shown by the arrows on the bottom half of the ellipse. As can be seen, when the excitatory stimulus is applied at certain times in the cycle, the state is urged towards the stable region. By carrying out this process repeatedly, the brain state is stabilized, and the seizure is brought to an end, or prevented entirely. What is demonstrated by FIG. 3B is that it is not only the amplitude, but the phase of the stimulus which is instrumental in producing the desired response.

Figure 4A:
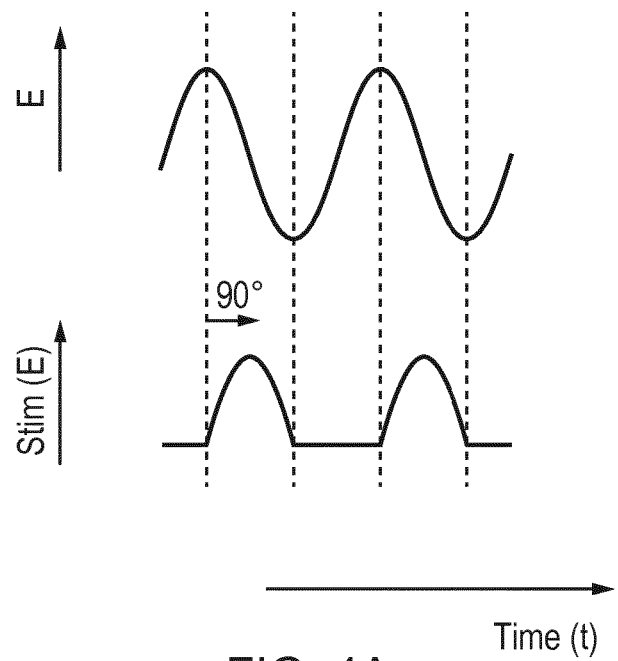
FIGS. 4A and 4B show plots of the stimulation applied to the target neurons, and the activity monitored by the sensor, varying with time.

This phase difference of the excitatory stimulus is shown more clearly in FIG. 4A, which compares a plot of the activity of the excitatory population and the applied stimulus, and how they change with time. For clarity, the excitatory population is shown here as sinusoidally-varying, but clearly this need not be the case. In the example shown in FIG. 4A, the excitatory stimulus is applied with a 90° phase shift, as compared with the excitatory population. The benefit of this may be seen from FIG. 4B. As well as being phase-shifted, the input signal (shown in the top plot) has also undergone thresholding/rectification. Hence, no stimulation is delivered to the target neurons during certain phases of the oscillation. This may be understood from the state space representation shown in FIG. 3B. The excitatory stimulus (of FIG. 3B) is applied only during the regions when the activity of the excitatory population is falling, i.e. on the lower half of the ellipse. It is during this stage of the oscillation that excitatory stimulation causes the activity of the excitatory population to increase, and thus move towards the target region. By applying the excitatory stimulus at during this phase of each oscillation, the state of the brain spirals in to the stable region of the plot. No stimulation is delivered during the stages where the activity of the excitatory population is increasing, i.e. at the upper half of the ellipse, since this would further destabilize the state of the brain and prolong the seizure.

Figure 4B:
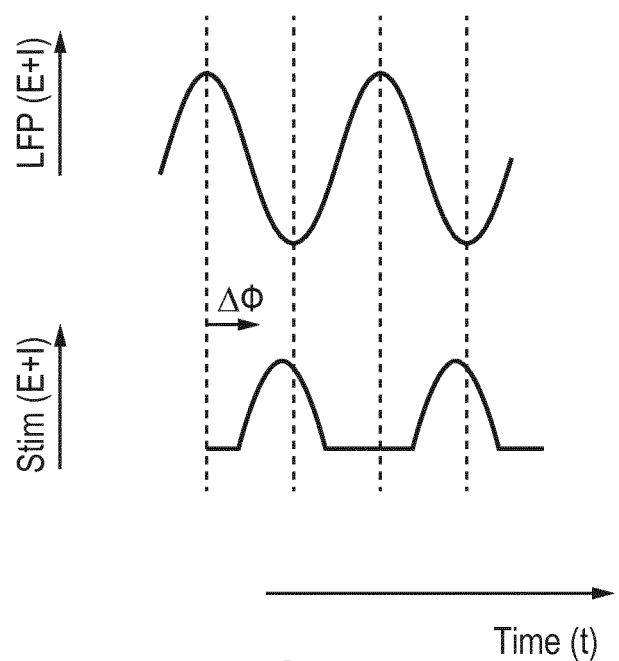

FIG. 4B shows a similar plot to FIG. 4A. In reality, it may be complex to measure the target activity of only the excitatory population. Instead, the LFP may be measured, which represents a combination of the activities of both the excitatory and inhibitory population. Similarly, the excitatory stimulation may excite neurons in both the inhibitory and excitatory population in some fixed proportion (i.e. the stimulation will cause a given state to move diagonally up and to the right, in the representation of FIG. 3B). Due to the contribution to the LFP of the inhibitory neurons, the LFP may be phase-shifted relative to just the activity of the excitatory population, and accordingly 90° may not be the ideal phase-shift. Rather, some phase shift $\Delta\phi$ may be more effective. This parameter, may be empirically determined, e.g. on a patient-by-patient basis, and may depend on the relative proportion of inhibitory and excitatory neurons in a given neural network. The results of experiments at different values of $\Delta\phi$ are discussed later in this application.

Figure 5A:
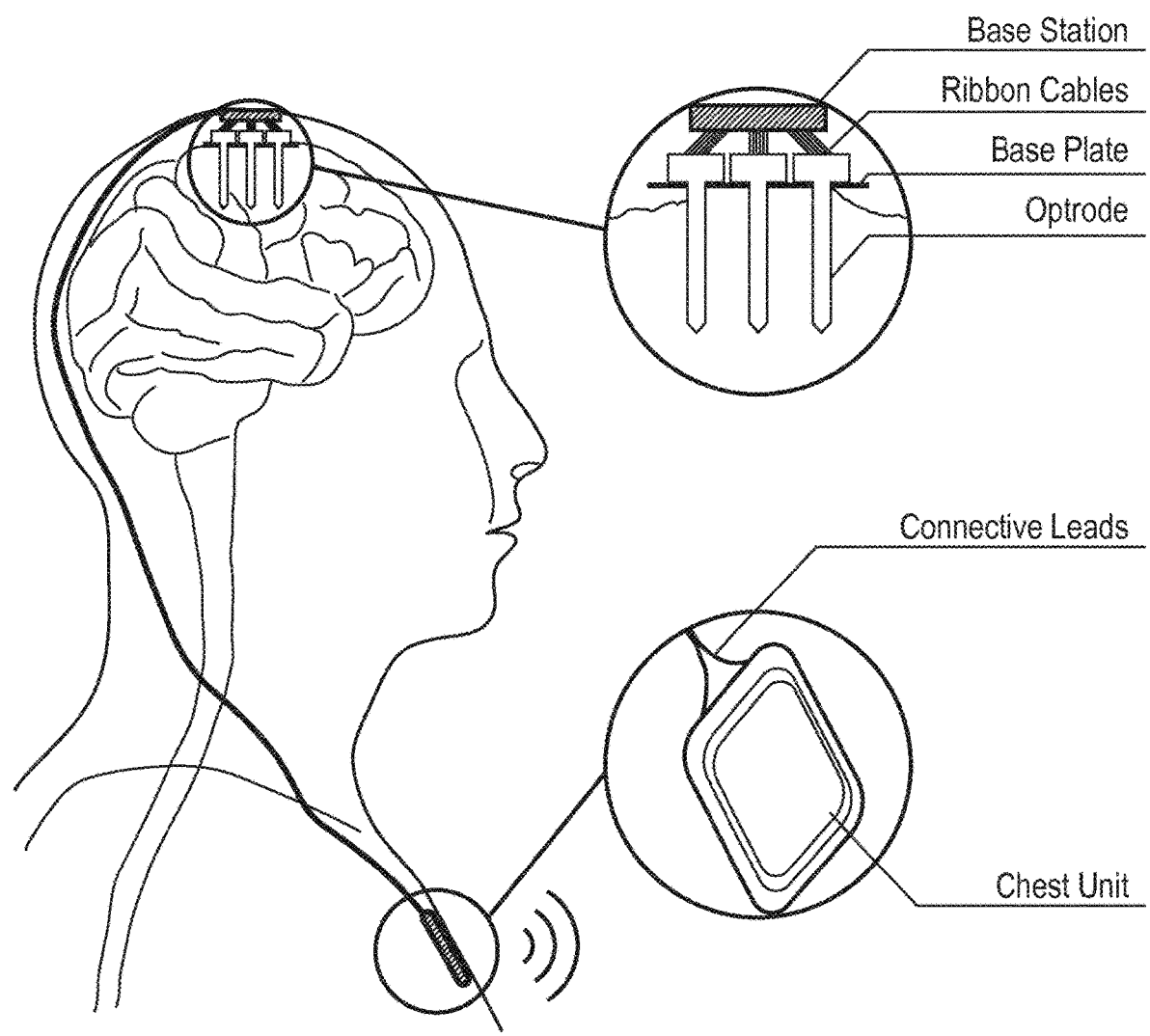
FIGS. 5A, 5B and 5C show an embodiment of the optogenetic system of the present invention.

FIG. 5A shows a diagram of an embodiment of the optogenetic system of the present invention in place in a patient or user. Here, the implantable device is in place in the user's brain tissue, with the optrodes (which are shafts with light-emitting elements and recording electrodes mounted thereon) extending into the brain tissue at the top of the head. The optrodes pass through a base plate, discussed in more detail with reference to FIG. 5C. Cables, e.g. ribbon cables, connect the end of the optrode (which is not implanted inside the brain tissue) to a base station located on the outside of the skull, which itself is connected to a chest unit via connecting leads. In use, the recording electrodes send the input signal to the chest unit via connecting leads to the chest unit. The chest unit contains the processor, which is used to process the input signal, and accordingly generate an output signal, which is then sent back to the optrodes via the connecting leads, in order to generate the desired signal in the form of an excitatory stimulus.

Figure 5B:
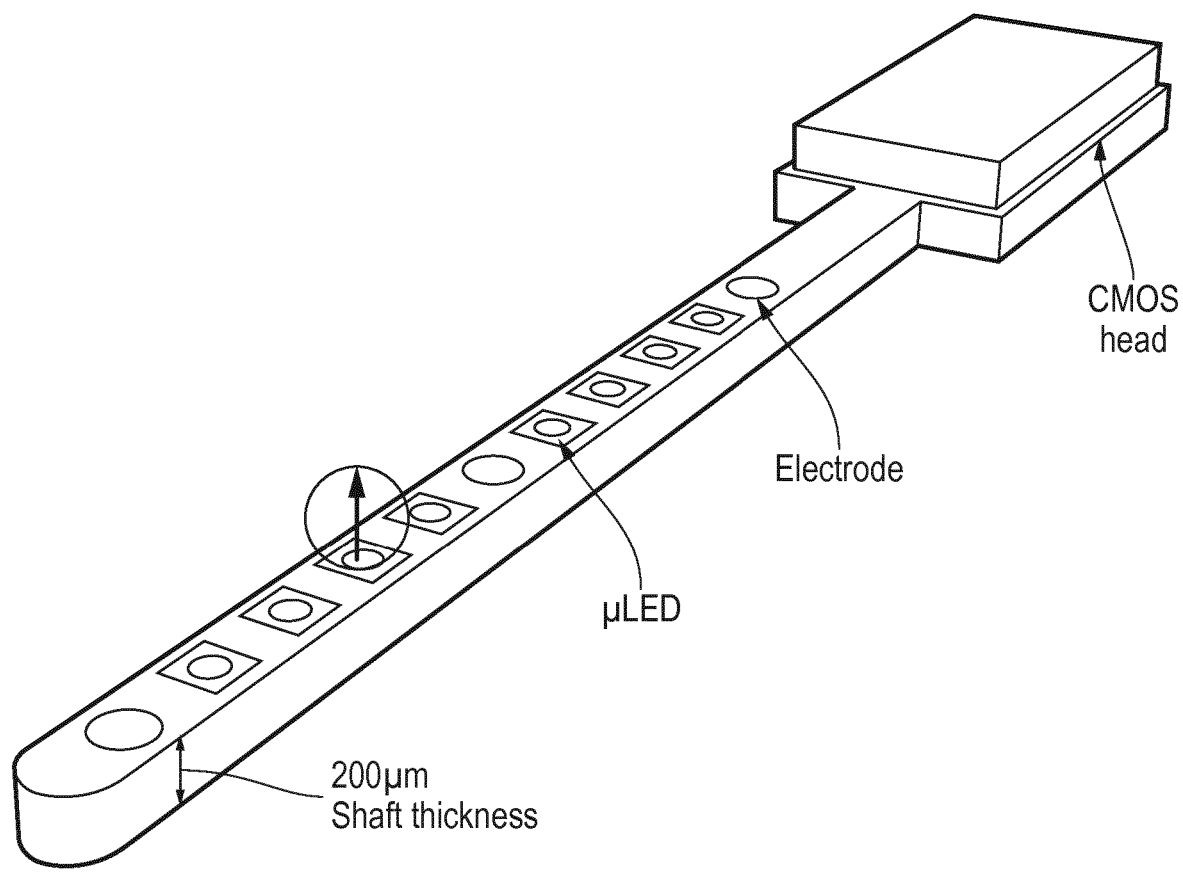

FIG. 5B shows a more detailed view of an optrode. The optrode is made up of two main components: the CMOS head and the shaft. The shaft is an elongate body, having a thickness of approximately 200 µm, in the present embodiment. Three recording electrodes are located on the shaft, along with eight µLEDs. The three electrodes are evenly-spaced, with the µLEDs located in the spaces between the recording electrodes, also evenly-spaced. Each of the recording electrodes and µLEDs are connected to the CMOS head, shown at the rear end of the shaft. The connections are preferably inside the shaft itself. The CMOS head includes electronics for processing the signals received, and for sending the signals to the chest unit. The CMOS unit is also configured to send the output signal to the µLEDs, in order to generate the optical signals forming the excitatory stimulus. There may be recording electrodes and µLEDs present on both sides of the shaft, but only one side is shown in FIG. 5B.

Figure 5C:
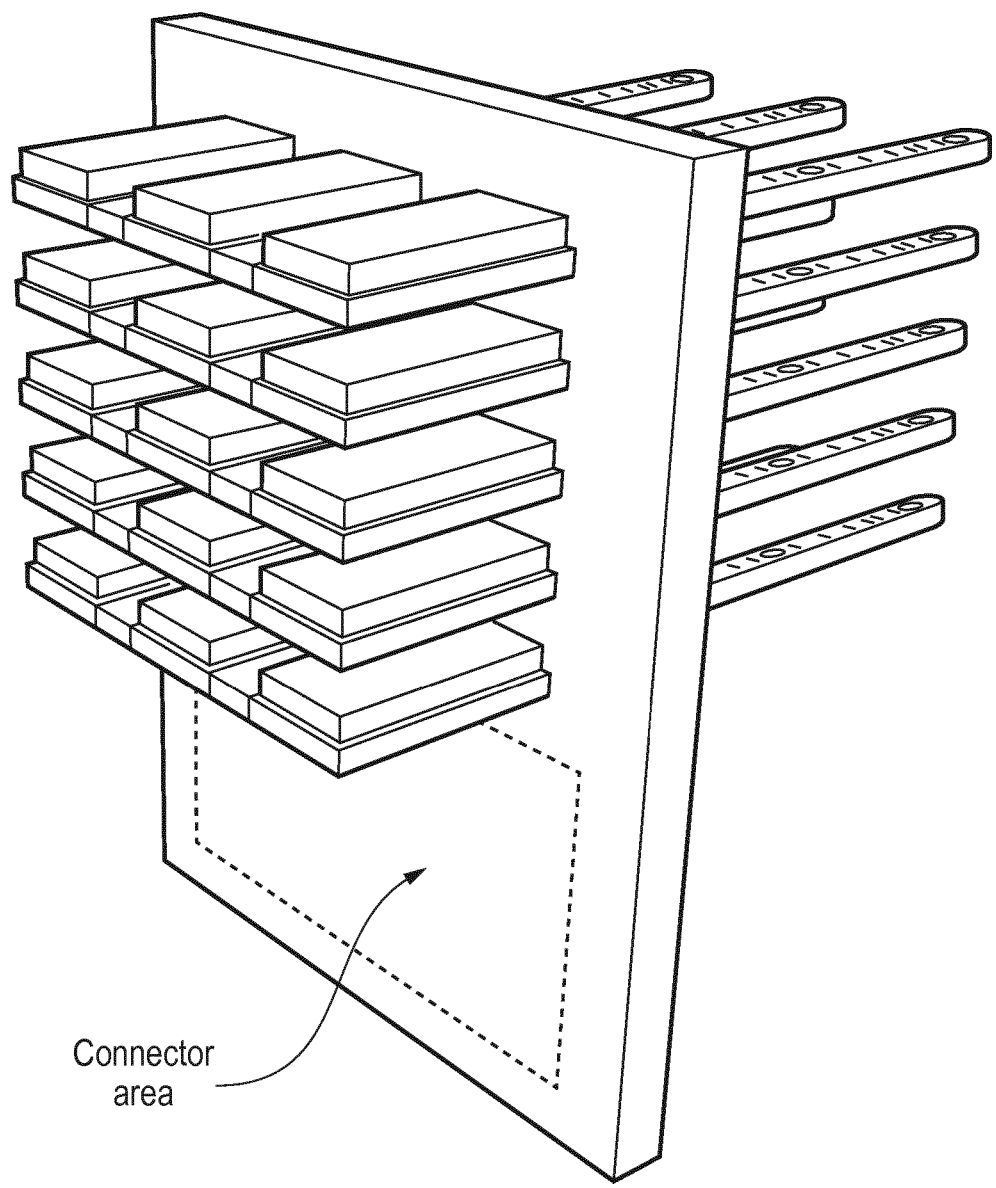

FIG. 5C shows the implantable device in more detail, with an array of fifteen optrodes in place. Specifically, each of the optrodes extends through an aperture in the base plate, with the shaft extending from one side, and the CMOS head at the other. A region of the base plate does not have any apertures, and acts as a connector area for connecting to a base station which, in use, is located on the outside of the skull. The base station may be connected to the CMOS heads of each of the optrodes, and also to the chest unit. In use, the shafts of the optrodes is located in the user's brain tissue, with the base plate, CMOS heads and base station located on the user's scalp.

FIGS. 6 to 9 show results of the experiment set up as described above.

Figure 7:
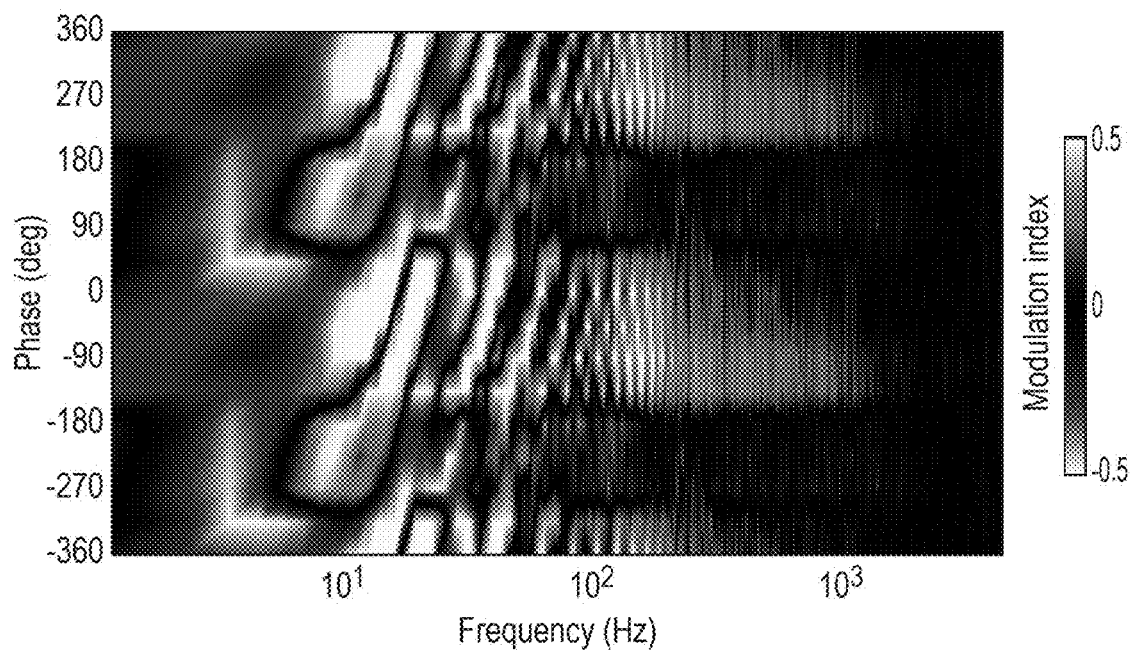
FIG. 7 shows a plot of power modulation for different frequencies and phase shifts of optical stimulation.

FIG. 6 shows several plots, in which SLEs are aligned to the time of onset. In the drawing, different traces are colour-coded to represent the different phase-shifts of the signals applied to the target neurons, relative to the input signal. Black traces indicate no stimulation. A key feature of these plots is the length of the oscillatory component of the seizures. In particular, it can be seen that relative to no simulation, some phase shifts significantly decrease the length of the seizure, while other phase shifts lengthen it. Similar effects are evident from FIGS. 7 to 9. Specifically, FIG. 7 shows the power modulation at different frequencies during the SLEs produced by closed-loop stimulation with different phase shifts. Phase is unwrapped and plotted twice up the vertical axis. Red indicates increased power relative to no stimulation, and blue indicates reduced power. Note the band of blue across high frequencies at a phase shift of 90-180°. High frequency stimulation delivered to excitatory neurons can reduce the overall activity within the slice, if delivered at an appropriate phase relative to spontaneous activity.

Figure 8:
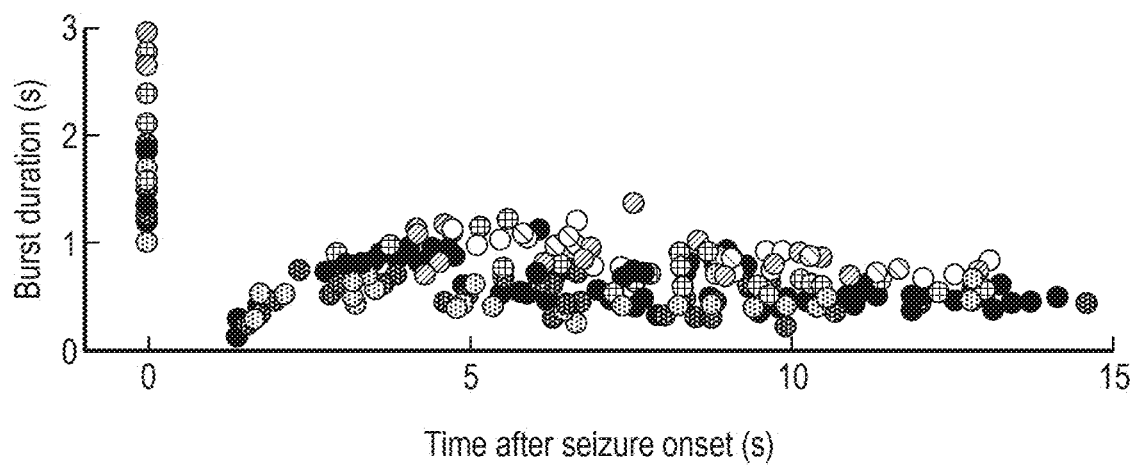
FIG. 8 shows a plot of the time after seizure onset against the burst duration, with the points colour-coded according to the phase shift of the applied optical stimulation.
Figure 9A:
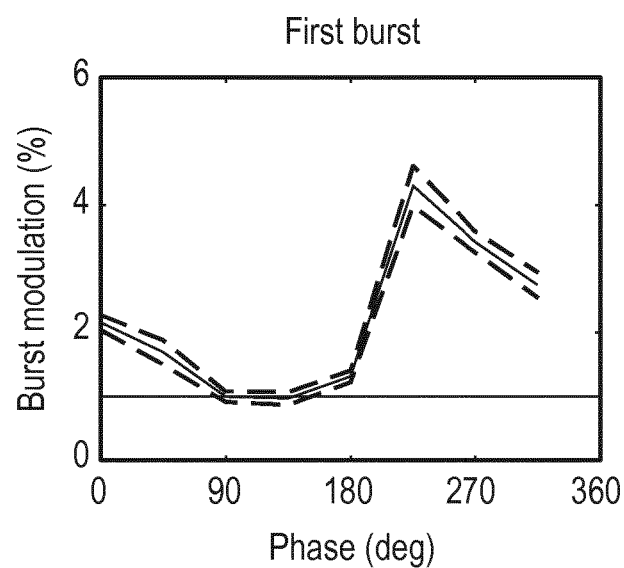
FIGS. 9A and 9B show plots of burst durations against the phase shift, for (A) the first burst, and (B) the subsequent bursts.
Figure 9B:
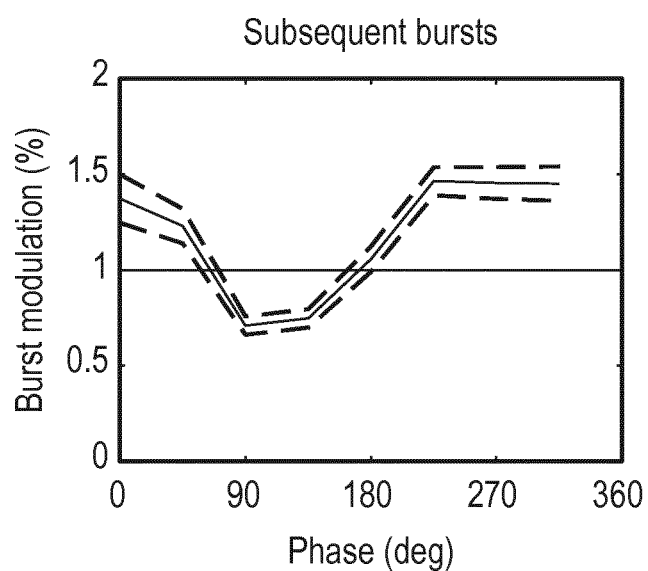

FIG. 8 shows a plot of the duration of bursts during SLEs. The dots are colour coded according to the phase shift of the applied stimulation, with the same colour code as for FIG. 1. Similarly, FIGS. 9A and 9B show plots of phase difference, and the burst modulation (i.e. the percentage during for stimulation on, relative to stimulation off, 100% means no effect, whereas 50% and 200% mean respectively that the duration is half and twice what it is without stimulation), for both the first burst of SLE activity, and subsequent bursts. It is shown that an stimulation tends to increase the length of the first burst, but for phase differences between 90 and 180°, this increase is smallest. Then, for all subsequent bursts, the duration is shortened (relative to no stimulation) for delivery of excitatory stimuli which differ in phase from the activity of the target neurons by 90 to 180°.

Below are described two exemplary sets of experiments, one in vitro and the other in silico that have been conducted by the inventors to demonstrate the phase-dependent modulation of epileptic activity using closed-loop optogenetic stimulation.

Example 1—Phase-Dependent Modulation of In Vitro Epileptic Activity Using Closed-Loop Optogenetic Stimulation This example considers phase-dependent modulation of epileptic activity using closed-loop optogenetics in rodent brain slices selectively expressing Channelrhodopsins-2 (ChR2) either in excitatory pyramidal neurons using an Emx1 promoter, or in a subset of inhibitory cells using the parvalbumin (PV) promoter.

Experimental Details

Brain Slice Preparation

Coronal neocortical brain slices (400 μm) were prepared from Emx1-ChR2 and PV-ChR2 mice, which provides selective neuronal expression of channelrhodopsin-2 in glutamatergic cells (Gorski et al., 2002[1]). The mice were perfused using the same ice-cold oxygenated (95% O2/5% CO2) sucrose-containing artificial cerebrospinal fluid (sACSF) used for cutting the brain slices; (sACSF in mm: 252 Sucrose, 24 NaHCO3, 2 MgSO4, 2 CaCl2, 10 glucose, 3.5 KCl, 1.25 NaH2PO4). Rodent brain slices were cut using a 5100 mz vibratome (Camden Instruments). The slices were later transferred and incubated at room temperature in a brain tissue interface holding chamber until later electrophysiological recordings. During recordings, the slices were perfused with the oxygenated normal ACSF (in mm: 126 NaCl, 24 NaHCO3, 1.2 MgSO4, 1.2 CaCl2), 10 glucose, 3 KCl, 1.25 and NaH2PO4) held at 33-34° C.

[1]Gorski J A, Talley T, Qiu M, Puelles L, Rubenstein J L, Jones K R (2002) Cortical excitatory neurons and glia, but not GABAergic neurons, are produced in the Emx1-expressing lineage. The Journal of neuroscience: the official journal of the Society for Neuroscience 22:6309-6314.

Electrophysiological Recording

To test the proposed closed-loop algorithm in vitro, local field potentials (LFP) from rodent brain slices were recorded, using these to control optical stimulation in a closed-loop manner. All the electrophysiological recordings were performed using an interface recording chamber and 16-channel linear multi-electrode array probe (NeuroNexus Technologies: A16×1-2 mm-100-177 probes—shanks are 100 μm apart; recording site area on each shank, 177). The recording sites on all shanks were located 50 μm from the tip of the electrode. Using this MEA probe, 1500 μm of brain tissue could be sampled at any time either in the same cortical layer or across cortical layers. The impedance of the MEA electrodes used ranged between 0.4-2 MΩ.

LFP signals were amplified using a MP8I headstage and PGA amplifier (Multichannel Systems) with a combined gain of ×1000, and sampled with a Micro1401-3 data acquisition box (CED, UK) at approx. 10 KHz and visualised using Spike2 software running on Windows (Win 7) computer.

Epileptiform Activity Patterns

The convulsant compound 4-aminopyridine (4-AP; 200 μM) was bath applied to induce epileptiform activity in rodent brain slices. Two patterns of spontaneous LFP activity were observed after 4AP application which we have termed 'interictal activity' and 'ictal burst activity'. 'Interictal activity' was characterised in the absence of optogenetic stimulation by generally flat LFP with only occasional LFP transients ('spikes') which did not develop into oscillations. Note that despite the absence of seizure-like events (SLEs), we call this 'interictal' due to the similarity between this pattern and interictal discharges observed in clinical recordings. 'Ictal burst activity' was characterised by intermittent LFP transients that developed into SLEs comprising multiple bursts of oscillatory activity. The difference between these patterns likely reflects inherent variability in the animals and/or brain slice preparations.

Closed-Loop Optogenetic Stimulation

Figure 10:
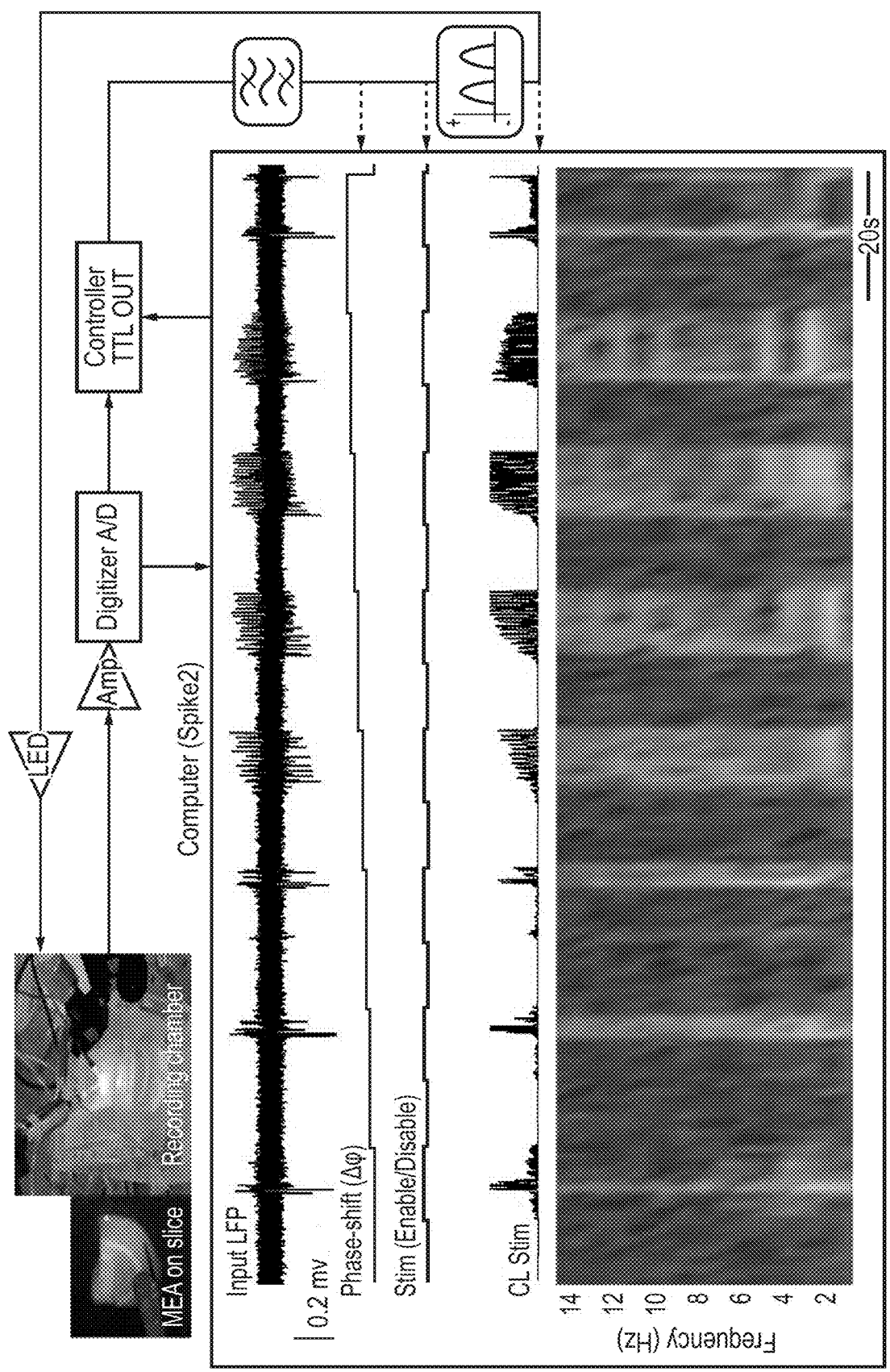
FIG. 10 is a schematic of closed-loop optogenetic experiment set-up.

Spike 2 software was used to select one of the acquired LFP channels as input to the closed-loop controller (FIG. 10). As seen in FIG. 10, the local field potential (LFP) recorded by one electrode is processed and fed-back via a real-time closed-loop algorithm to modulation an LED light source. An experimental session comprises periods of closed-loop stimulation using different phase-shifts, as well as interspersed periods with no stimulation.

More specifically, the output of the controller was a 0-5V voltage signal sent to an external LED driver (DC4104; Thorlabs) using the appropriate cable (CAB-LEDD1; Thorlabs). The LED driver was configured such that the 0-5V voltage range was converted to a constant current range of 0-1000 mA. This current drove a blue LED light source (473 nm, M470F1; Thorlabs) coupled to a 200 μm diameter optical fibre (M89L01-200; Thorlabs). The LED driver DC4014 was connected to the LED light source M470F1 via the DC4100-HUB connector hub from Thorlabs. For control experiments, we used a different wavelength of light source (590 nm, 590F2; Thorlabs), which falls outside the activation spectrum of ChR2 opsins.

Closed-Loop Algorithm

Figure 11:
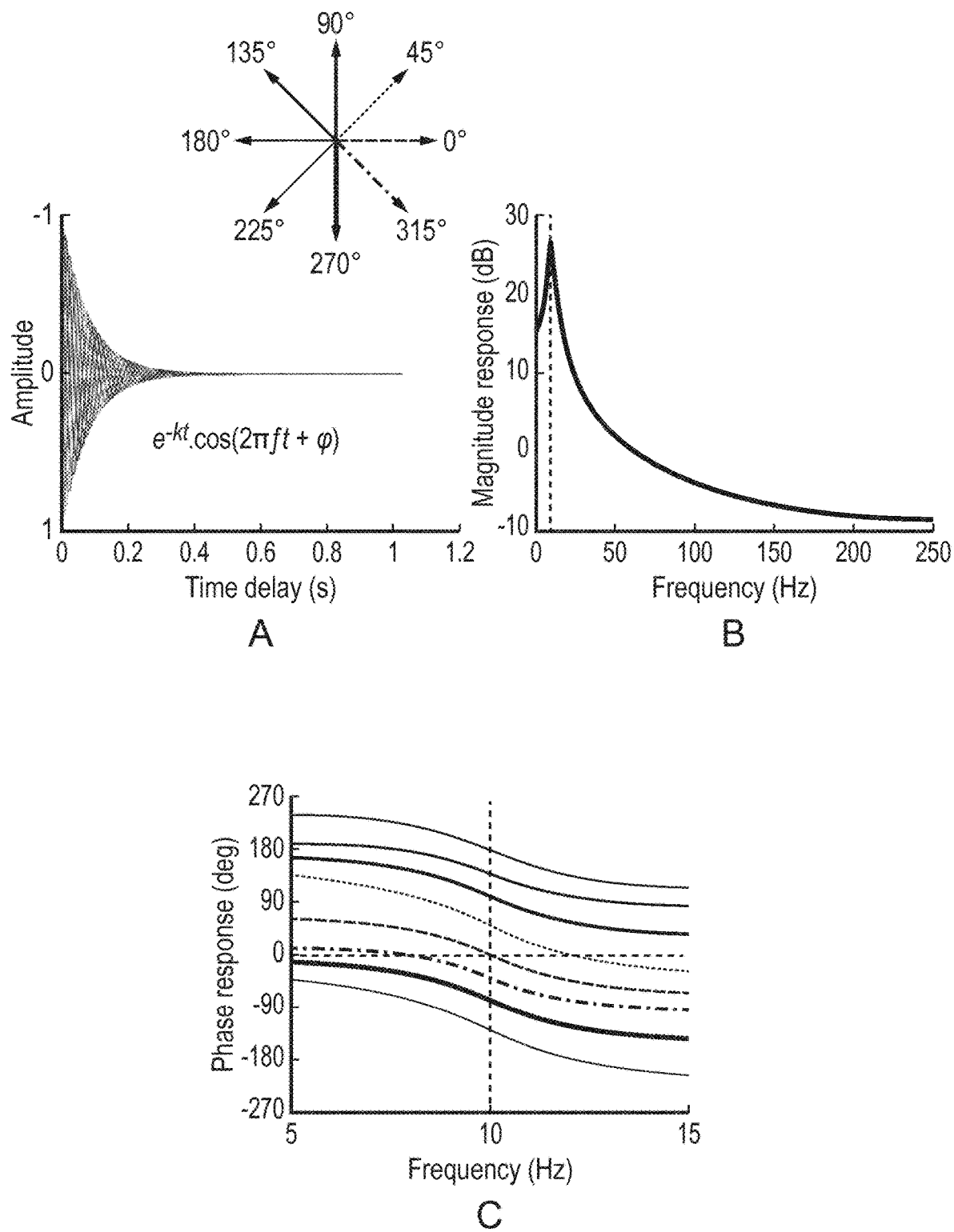
FIG. 11 shows, for an exemplary closed loop algorithm: A Example filter kernels used for filtering the LFP. Here the band-pass centre frequency is 10 Hz. B Gain response of the filter. C Phase response across the pass-band.

The closed-loop algorithm was implemented in custom-designed hardware based around a PIC dsPIC30F4013 microcontroller running at 30 MHz. The microcontroller sampled the LFP signal from one electrode at 500 Hz, applied a phase-shifting finite impulse response (FIR) filter, thresholded (above the background noise level) and half-wave rectified this signal to generate an output which controlled the LED intensity. The FIR filter convolved the input signal with a kernel given by:

$$e^{-kt} \cdot \cos(2\pi ft + \varphi)$$

where k determines the filter band-width and was equal to 1.25; φ determines the extent to which the output is phase-advanced from the input and cycled from 0 to 315° in 45° steps; f determines the center frequency of the pass-band and we used different values in different experiments. In general we chose f to reflect the dominant frequency of 'ictal burst activity' (10-20 Hz), and for 'inter-ictal' recordings, we chose frequencies between 2-20 Hz. The total kernel length was 512 samples. FIG. 11 shows typical filter kernals used, as well as the resultant gain profile and phase-shifts. The overall gain of the closed-loop algorithm was chosen such that typical seizure activity resulted in a full-scale activation of the LED light source, with minimal saturation.

Experiments comprised periods of closed-loop stimulation (LED On) and periods of no stimulation (LED Off). For 'ictal burst recordings', the duration of these periods was adjusted to ensure that generally at least one spontaneous seizure occurred during each duration.

Analysis

Data were analysed using custom scripts written in Matlab (Mathworks, USA). For 'interictal activity', frequency-domain analysis was performed on the entire period of each stimulation condition. For 'Ictal burst activity' we analysed only time-periods containing SLEs. The onset of each SLR was identified by an initial threshold crossing below −0.3 mV. Analysis was performed only for a time window of 18 s, chosen to capture the duration of SLEs. In each case, average power spectra for the LFP signal were compiled over the relevant time periods for each condition. Power modulation was calculated as a ratio (in decibels) relative to power during LED Off periods.

In addition, the duration of seizure bursts within SLEs was calculated. The LFP was first high-pass filtered (at 8 Hz) and rectified the LFP. A burst was defined as any time-period for which this signal was not less than 0.1 mV for more than 0.2 s. Bursts with a duration less than 10 ms were excluded. Because the duration of the first burst within the SLE was typically longer than subsequent bursts, these were analysed separately.

Results and Discussion

Excitation of Glutamatergic Pyramidal Neurons During 'Interictal Activity'

Figure 12:
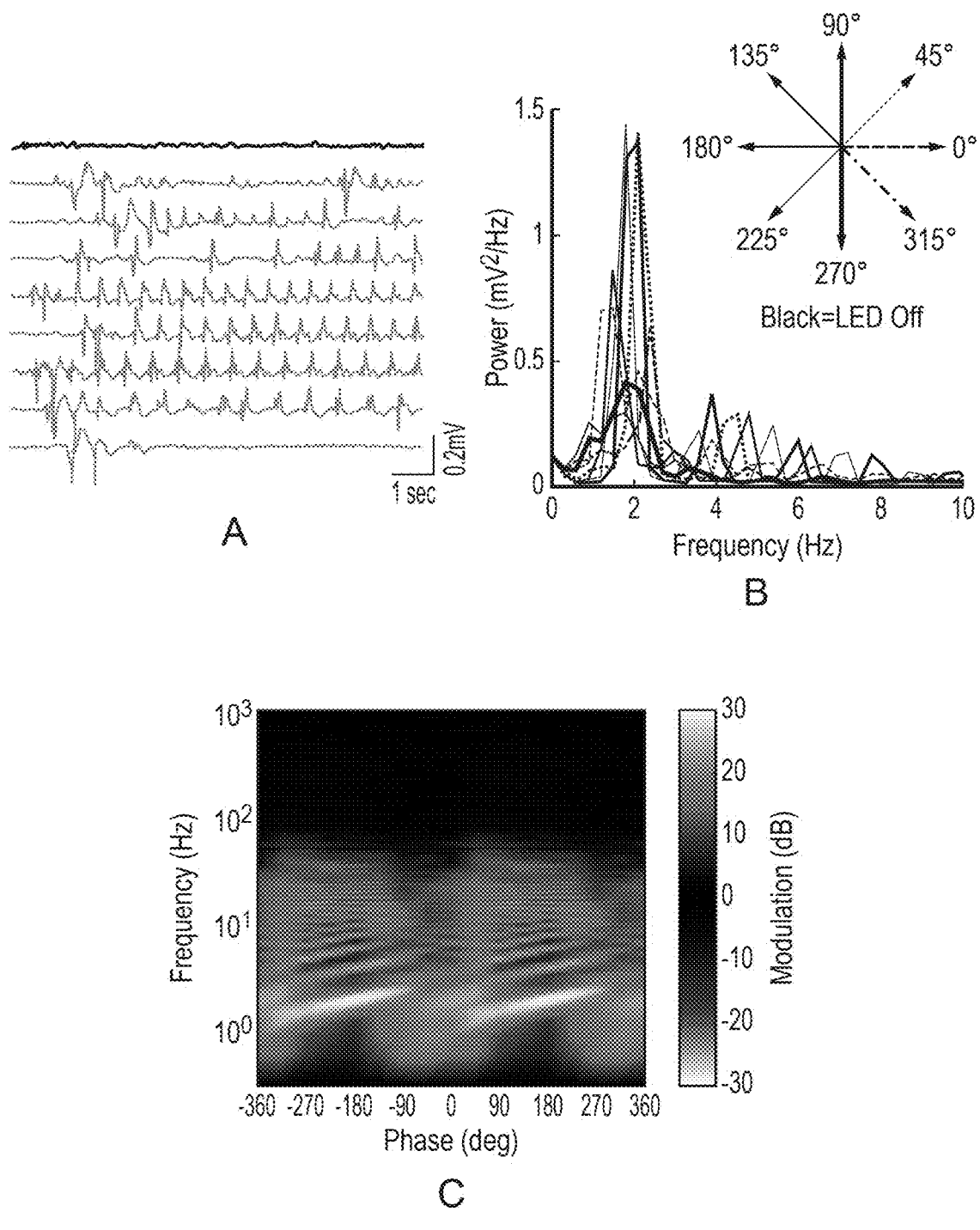
FIG. 12 shows plots relating to the generation of rhythmical LFP oscillations by closed-loop optogenetic stimulation in neocortical slices from EMX-ChR2 mice.

In neocortical slices from Emx1-ChRs mice which did not exhibit spontaneous SLEs ('interictal activity'), closed-loop optogenetic stimulation could reliably elicit rhythmical LFP oscillations (FIG. 12). In FIG. 12, A shows example traces with no stimulation and during closed-loop stimulation with different phase-shifts; B shows LFP power spectra for different stimulation conditions; and C shows power modulation (relative to LED-Off) as a function of frequency and phase-shift. Note that phase is unwrapped and plotted over two cycles. In this case, closed-loop stimulation generated an oscillation with a fundamental frequency that increased with increasing phase-shift.

In general, these oscillations resulted from a spontaneous large amplitude spike which was fed back by the closed-loop algorithm. We found that the fundamental frequency of the oscillations (and the higher harmonics) increased with increasing phase-shift. Note that by convention we denote positive phase-shifts as a phase-advance of the output relative to the input. Therefore we can alternatively consider that the frequency of oscillation decreased with increasing phase-delay of the (output) optical stimulation relative to the (input) LFP. This makes intuitive sense since the stimulation resulting from a brief LFP spike will resemble the impulse response of the filter. Thus, the peaks of this impulse response (and hence the timing of optical stimulation) will occur later with increasing phase-delay, leading to a slower oscillation. Note also that the amplitude of the induced oscillation varied with stimulation condition, and was greatest when the phase-shift generated a frequency of oscillation that matched the pass-band of the filter, while at other frequencies the closed-loop stimulation did not generate sustained oscillatory activity. However, since the 'interictal activity' was characterised by an absence of oscillatory activity in the LED off condition, a general increase in LFP power was observed in all stimulation conditions.

Excitation of Glutamatergic Pyramidal Neurons During 'Ictal Burst Activity'

Figure 13:
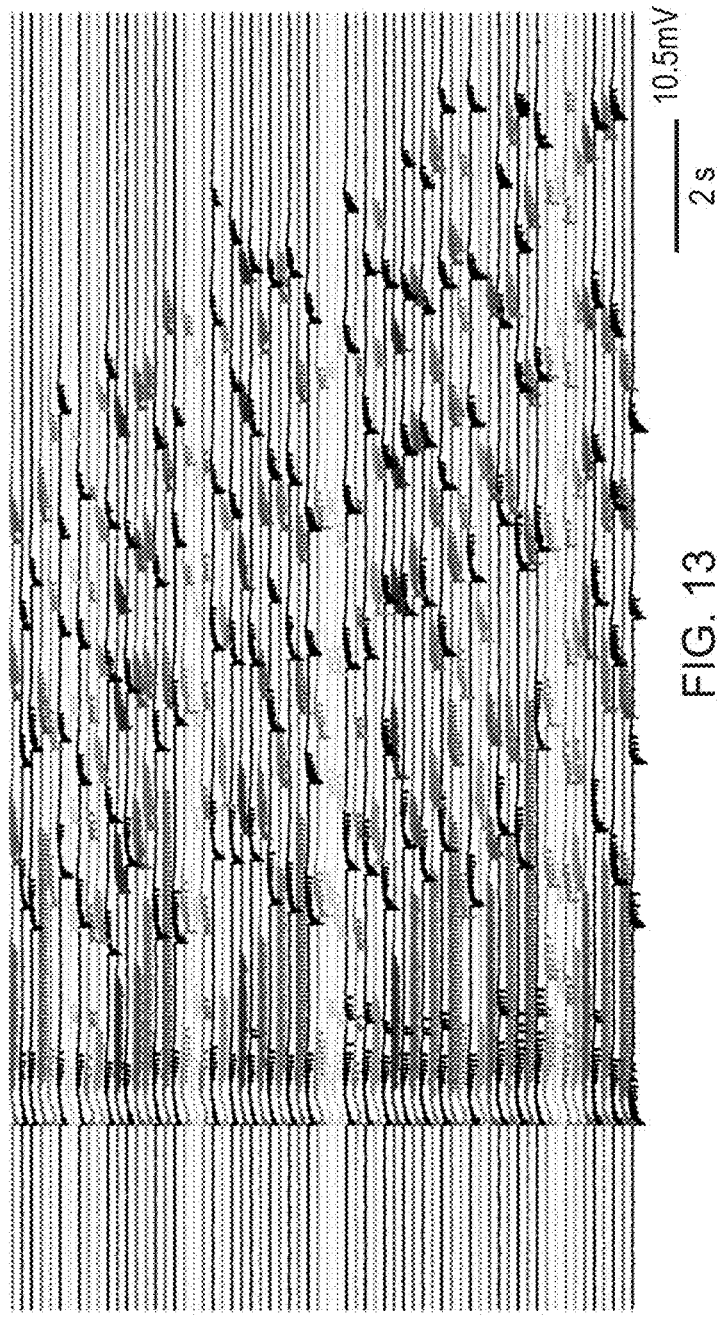
FIG. 13 shows a plot for optogenetic modulation of SLE durations by closed-loop optogenetic stimulation in neocortical slices of EMX-ChR2 mice.

Also examined was the effect of closed-loop optical stimulation of pyramidal neurons in the case that spontaneous SLEs were induced by 4-AP. FIG. 13 shows all SLEs observed in a single experimental session, aligned to the event onset and colour-coded according to stimulation condition (see FIG. 14). In this recording, SLEs consisted of an initial negative deflection followed by a burst of oscillation at around 15-20 Hz lasting a few seconds. After a period of quiescence, subsequent bursts were seen. Each entire SLE lasted about 18 s and occurred with an inter-event interval of approximately 1 minute. Interestingly, closer inspection of the SLEs (FIG. 14) suggests that the duration of the oscillatory bursts varied with closed-loop stimulation condition.

Figure 15:
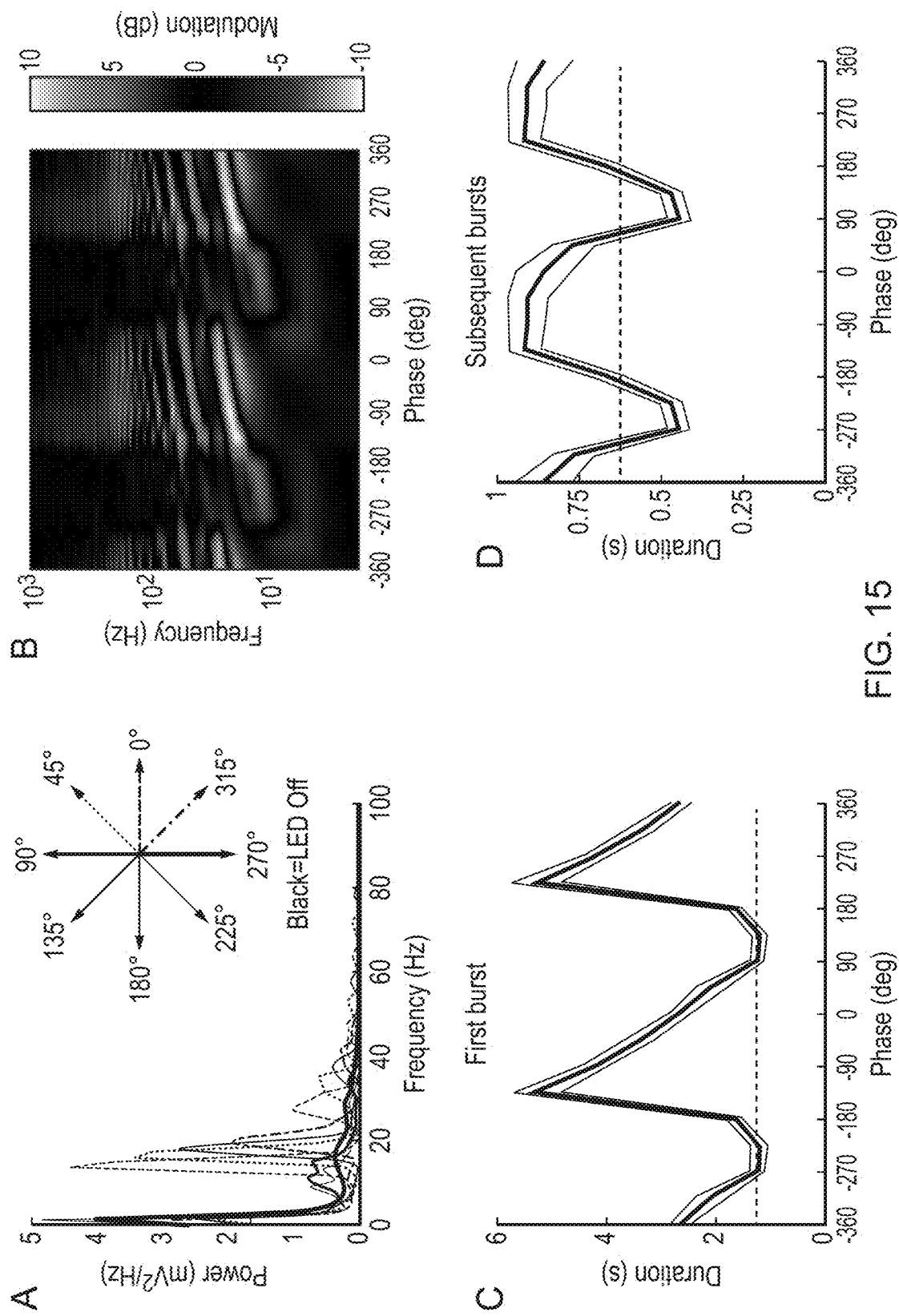
FIG. 15 is a plot showing that closed-loop stimulation of excitatory network reduces high frequency power of the shortened SLEs during 90-180° phase-shifts.

FIG. 15A shows power-spectra for SLEs divided according to stimulus condition, and FIG. 15B shows the modulation of power at each frequency relative to the LED Off condition as a function of the phase-shift applied by the closed-loop algorithm. Again it is clear that some phase-shifts induce a pronounced oscillation with a fundamental frequency (and higher harmonics) that increased with increasing phase-advance (or decreasing phase-delay). Note however that since there was spontaneous activity in the LED Off condition, closed-loop stimulation could either increase or decrease power at different frequencies depending on the phase-shift used. Phase-shifts between 90-180° resulted in reduced power at the dominant frequency of the spontaneous SLEs (15-20 Hz). Interestingly these phase conditions also led to a reduction in power at higher frequencies up to 1000 Hz in the LFP. These higher frequencies are thought to reflect the spiking activity of local neurons, including the pattern of recruitment of neurons to seizures recorded in human patients (Schevon et al., 2012; Weiss et al., 2013[2]). Therefore it appears that excitatory stimulation, delivered selectively to excitatory cells, could nevertheless result in a net reduction of activity during SLEs when timed appropriately to the ongoing seizure oscillation.

[2]Schevon C A, Weiss S A, McKhann G Jr, Goodman R R, Yuste R, Emerson R G, Trevelyan A J (2012) Evidence of an inhibitory restraint of seizure activity in humans. Nature Communications 3:1060

The duration of oscillatory bursts within each SLE was also examined. The duration of the first burst within the SLE was either unchanged or extended depending on closed-loop phase-shift (15C). However, the duration of subsequent bursts was suppressed for phase-shifts between 90-180° (15D) (the same conditions associated with a broad reduction in LFP power). In FIGS. 15C and 15D, the red dashed line shows average duration in LED Off condition. Shading indicates s.e.m. Note that phase-shifts associated with higher/lower LFP power are also associated with longer/shorter oscillatory bursts.

Example 2—Phase-Dependent Modulation of in Silico Epileptic Activity Using Closed-Loop Stimulation This example considers computational modelling work that parallels the in vitro closed-loop optogenetic stimulation experiments discussed above.

Methods

Modelling Epileptiform Activity

The model used here is a variant of the classic Wilson-Cowan neural population model [Wilson and Cowan, 1972[3]], which is described in detail in previous publications [Wang et al., 2012, Wang et al., 2014[4]]. The two-variable version of it is used, which models the neural tissue as a single excitatory population and a single inhibitory population. This model is able to capture epileptiform spikes and epileptiform discharges [Wang et al., 2012[5]], which are the two key activity types from the experimental data.

[3]Wilson, H. and Cowan, J. (1972). Excitatory and inhibitory interactions in localized populations of model neurons. Biophysical Journal, 12(1):1-24
[4]Wang, Y., Goodfellow, M., Taylor, P. N., and Baier, G. (2014). Dynamic Mechanisms of Neocortical Focal Seizure Onset. PLoS Comput Biol, 10(8): e1003787
[5]Wang, Y., Goodfellow, M., Taylor, P., and Baier, G. (2012). Phase space approach for modeling of epileptic dynamics. Phys Rev E, 85(6):061918

Briefly, the differential equation system used is:

$$\frac{dE}{dt} = (-E + Sigm(a*E - b*I + P))/\tau_e \quad (1)$$

$$\frac{dI}{dt} = (-I + Sigm(c*E - d*I + Q))/\tau_i$$

where E (I) is the activity of the excitatory (inhibitory) neural population. The parameters a; b; c; d determine how strongly each population influences themselves and the other population. The parameters $\tau_e$ and $\tau_i$ are time constants, dictating how quickly a population reacts to incoming input.

Finally the sigmoid function is:

$$Sigm(x) = \frac{1}{1 + \exp(-(x-4))}.$$

This system will be simulated with noise of amplitude na (reflecting synaptic noise and non-specific input from the surrounding tissue). In other words, the Euler-Maruyama solver can be used to simulate the system as a stochastic differential equation system.

Depending on the parameter settings, the above described system is able to simulate epileptiform interictal spikes, similar to those observed in the in vitro experiments. Essentially, two parameter settings were used, one for the interictal spikes, and one for the ictal discharges. Table 1 lists these in detail for each configuration (interictal vs. ictal) in this example.

TABLE 1

|   | Interictal | Ictal |
|---|---|---|
| a | 17 | 17 |
| b | 15 | 10 |
| c | 40 | 40 |
| d | 0 | 0 |
| $\tau_e$ | 0.06 | 0.0264 |
| $\tau_i$ | 0.06 | 0.012 |
| P | 0 | −0.3 |
| Q | −7 | −15 |

Figure 16:
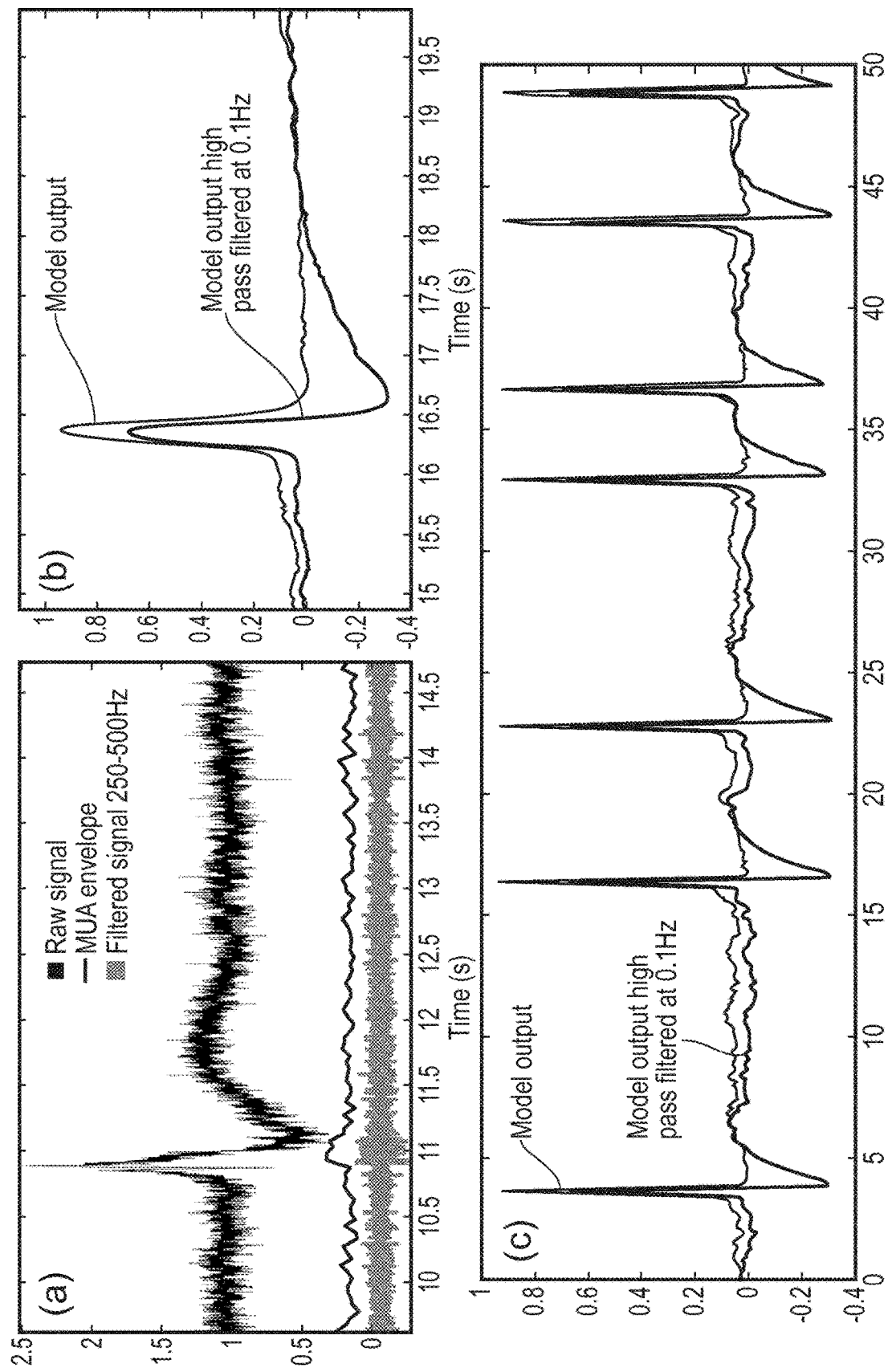
FIG. 16 shows plots of Epileptiform interictal spikes in a 4AP in vitro model and in a computational model.

FIG. 16 (a) shows an example of an epileptiform interictal spike from the in vitro experiments. FIG. 16 (b) in comparison, shows a simulated interictal spike from the model. It is important to note here that the spiking activity arises spontaneously in the model as a result of the noise input. FIG. 16 (c) shows a longer simulation with many spontaneous spikes. In dynamical systems terms, the system is in a stable node, with a homoclinic bifurcation (of the saddle and a limit cycle) nearby in parameter space (bifurcation parameter P). Hence the spike can be found as an excitable transient in phase space, and the added noise can occasionally perturb the system onto this transient. This mechanism has been used before in several studies to model interictal spikes, e.g. [Wendling et al., 2002[6], Wang et al., 2012]

[6]Wendling, F., Bartolomei, F., Bellanger, J., and Chau-vel, P. (2002). Epileptic fast activity can be explained by a model of impaired GABAergic dendritic inhibition. European Journal of Neuroscience, 15(9):1499-1508

The model outputs (E(t) and I(t)) is suggested to reflect the multi unit activity (MUA) in the in vitro recordings, whereas the local field potential (LFP) is perhaps best modelled as $hf_{0.1}(E+I)$. The hf( ) function is a high pass filter, in this case with a cut-off frequency of 0.1 Hz. This is to simulate the high-pass filtering properties of the in vitro recording equipment. Such a filter introduced slow waves after the spike, which resembled those observed in the in vitro recording (FIG. 16). In the strict sense, the modelling of the LFP should be an explicit part of the differential equations, as for example in the Jansen-Rit model [Jansen and Rit, 1995[7]]. In the Wilson-Cowan approach, this has been neglected, hence a simple E+I is assumed to represent the LFP.

[7]Jansen, B. and Rit, V. (1995). Electroencephalogram and visual evoked potential generation in a mathematical model of coupled cortical columns. Biological Cybernetics, 73(4):357-366

Figure 17:
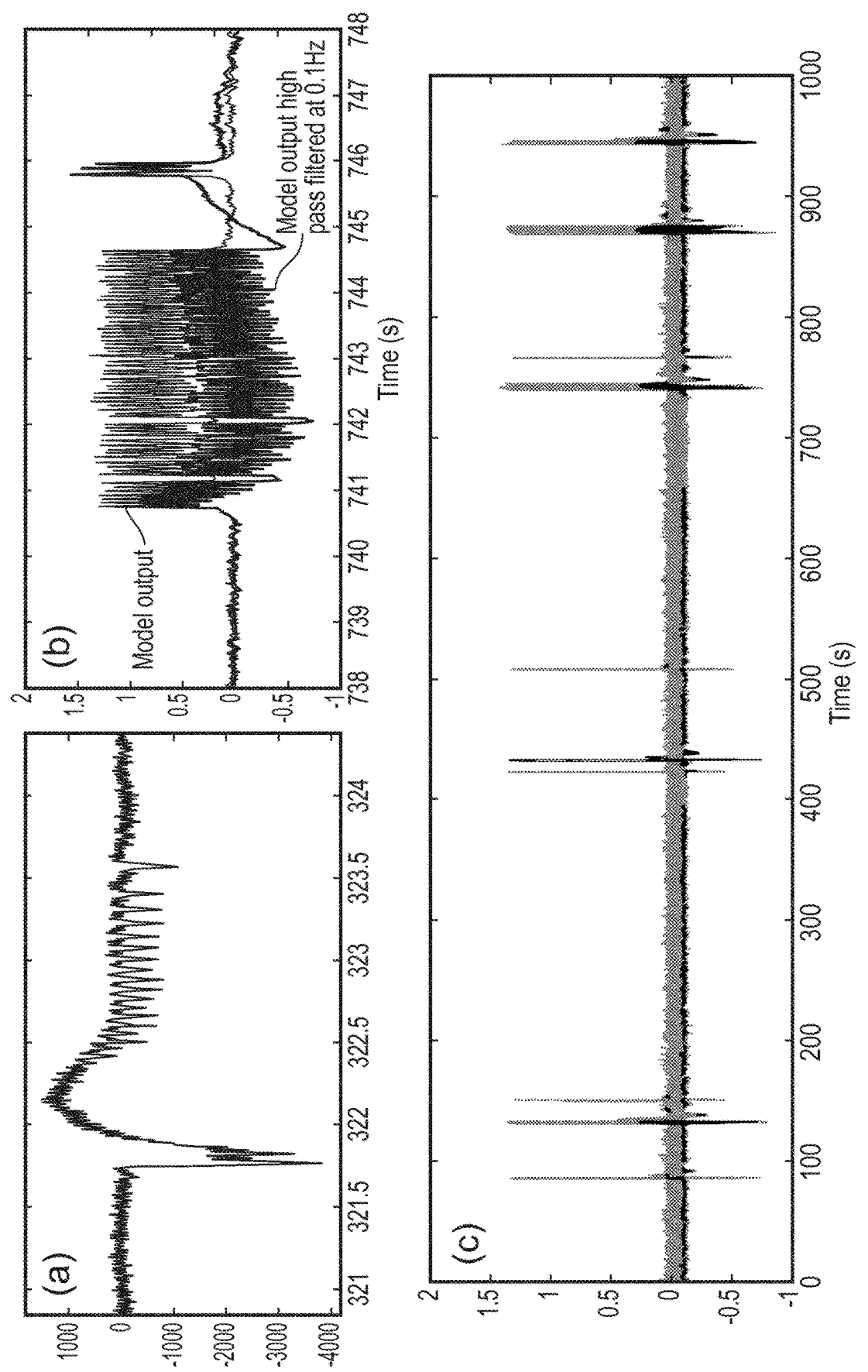
FIG. 17 shows plots of Epileptiform ictal discharge in the 4AP in vitro model and in the computational model.

Analogous to the modelling of spikes, the system described by equation 1 is capable of producing transient epileptiform ictal discharges, similar to those observed in the in vitro experiments. FIG. 17 (a) shows an example of an epileptiform ictal discharge from the in vitro experiments. FIG. 17 (b) in comparison, shows a simulated ictal discharge from the computational model. It is important to note here that the entire ictal discharge arises spontaneously in the model as a result of the noise input. FIG. 17 (c) shows a longer simulation with many spontaneous spikes. In dynamical systems terms, the system is in a stable node, with a coexisting bistable limit cycle (separated by the separatrix of a saddle in phase space). The noise input can then drive this system to and from the limit cycle, leading to the appearance of transient ictal discharges in the simulated time series. This bistability mechanism has been a popular one to model seizures [Lopes Da Silva et al., 2003[8], Breakspear et al., 2006[9], Wang et al., 2014].

[8]Lopes Da Silva, F., Blanes, W., Kalitzin, S., Parra, J., Su czynski, P., and Velis, D. (2003). Epilepsies as dynamical diseases of brain systems: basic models of the transition between normal and epileptic activity. Epilepsia, 44:72-83

[9]Breakspear, M., Roberts, J., Terry, J., Rodrigues, S., Mahant, N., and Robinson, P. (2006). A unifying explanation of primary gen-eralized seizures through nonlinear brain modeling and bifurcation analysis. Cereb Cortex, 16(9):1296-1313

Modelling Closed-Loop Stimulation

To model optogenetic input to the system, a simple approach was chosen. The light input is simply added as an additional input term modified by a weight I:

$$\frac{dE}{dt} = (-E + Sigm(a*E - b*I + P + l*LED(t)))/\tau_e \quad (2)$$

$$\frac{dI}{dt} = (-I + Sigm(c*E - d*I + Q))/\tau_i$$

The detailed dynamics of the Channelrhodopsin [Grossman et al., 2011[10]] and the subsequent conversion of this signal to a corresponding postsynaptic potential are simplified here. It is assumed that the LED input is proportional to its equivalent population input.

[10]Grossman, N., Nikolic, K., Toumazou, C., and Dege-naar, P. (2011). Modeling Study of the Light Stimulation of a Neuron Cell With Channelrhodopsin-2 Mutants. IEEE Transactions on Biomedical Engineering, 58(6): 1742-1751

In the experimental closed-loop system, the output of LED(t) is determined by the recorded ongoing activity of the slice. As described earlier, this is currently essentially a phase shifted, rectified version of the filtered recording. In the model, the same algorithm was followed as in the in vitro experiments. In the simulations, the term LED(t) is evaluated at each time point of the Euler-Maruyama algorithm that solves the SDE equations. As the recorded signal (i.e. the simulated LFP), a linear combination of E(t) and I(t) was used, as the real LFP will be a linear combination of population EPSPs and IPSPs, depending on the recording location.

Results

Interictal Spike Activity

Figure 18:
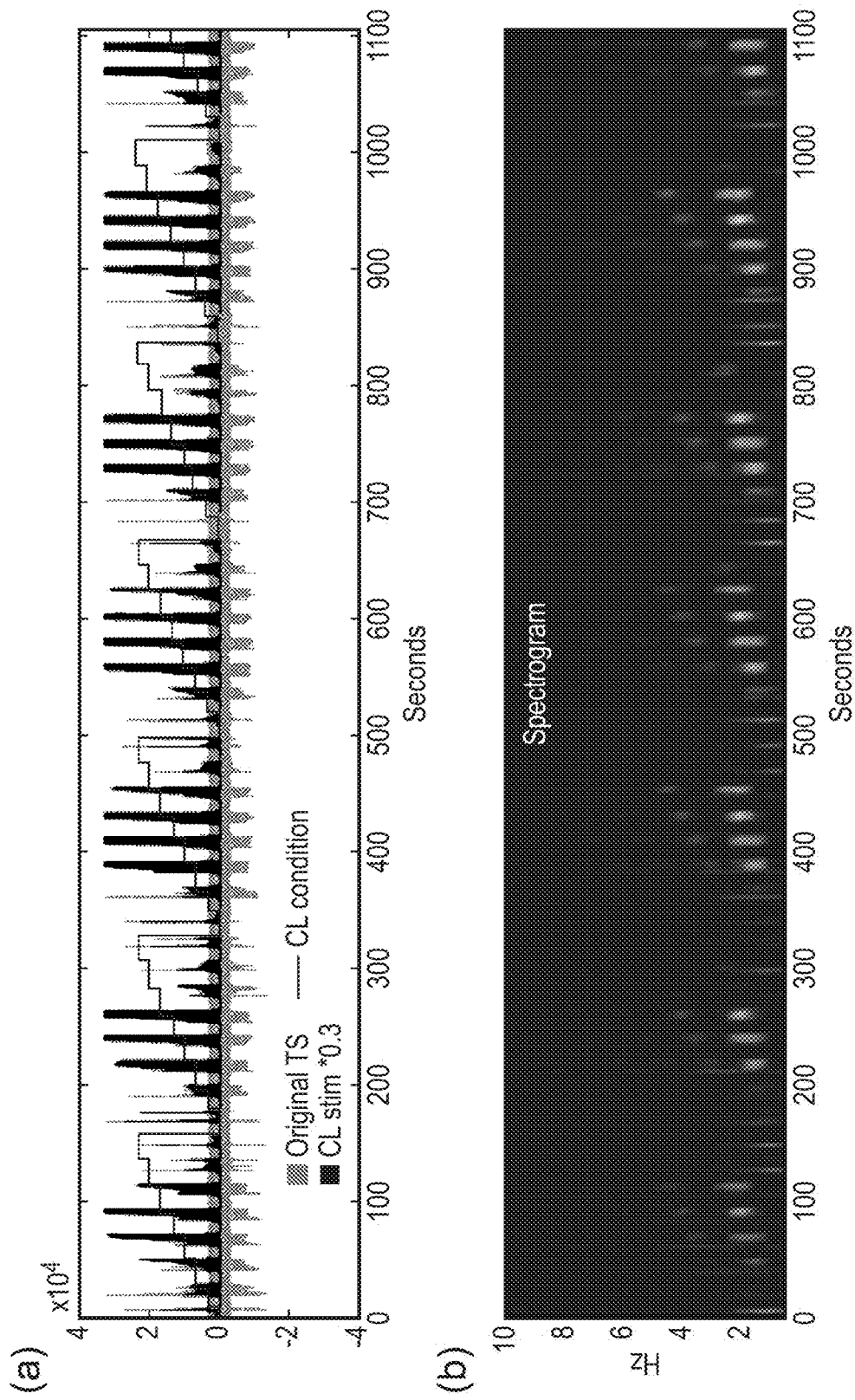
FIG. 18 shows plots from an example closed-loop stimulation on interictal spikes in vitro—(a) Several cycles of closed-loop stimulation with 8 phase conditions (0:45:315 degrees) shown in yellow. Grey is the recorded LFP time series, red shows the LED output signal. Each phase condition lasted 20 seconds. The LED was only switched on halfway through each phase condition. (b) Spectrogram of the recorded LFP time series in (a). (c) Zoom-in of a 90 degrees phase condition from (a).
Figure 18:
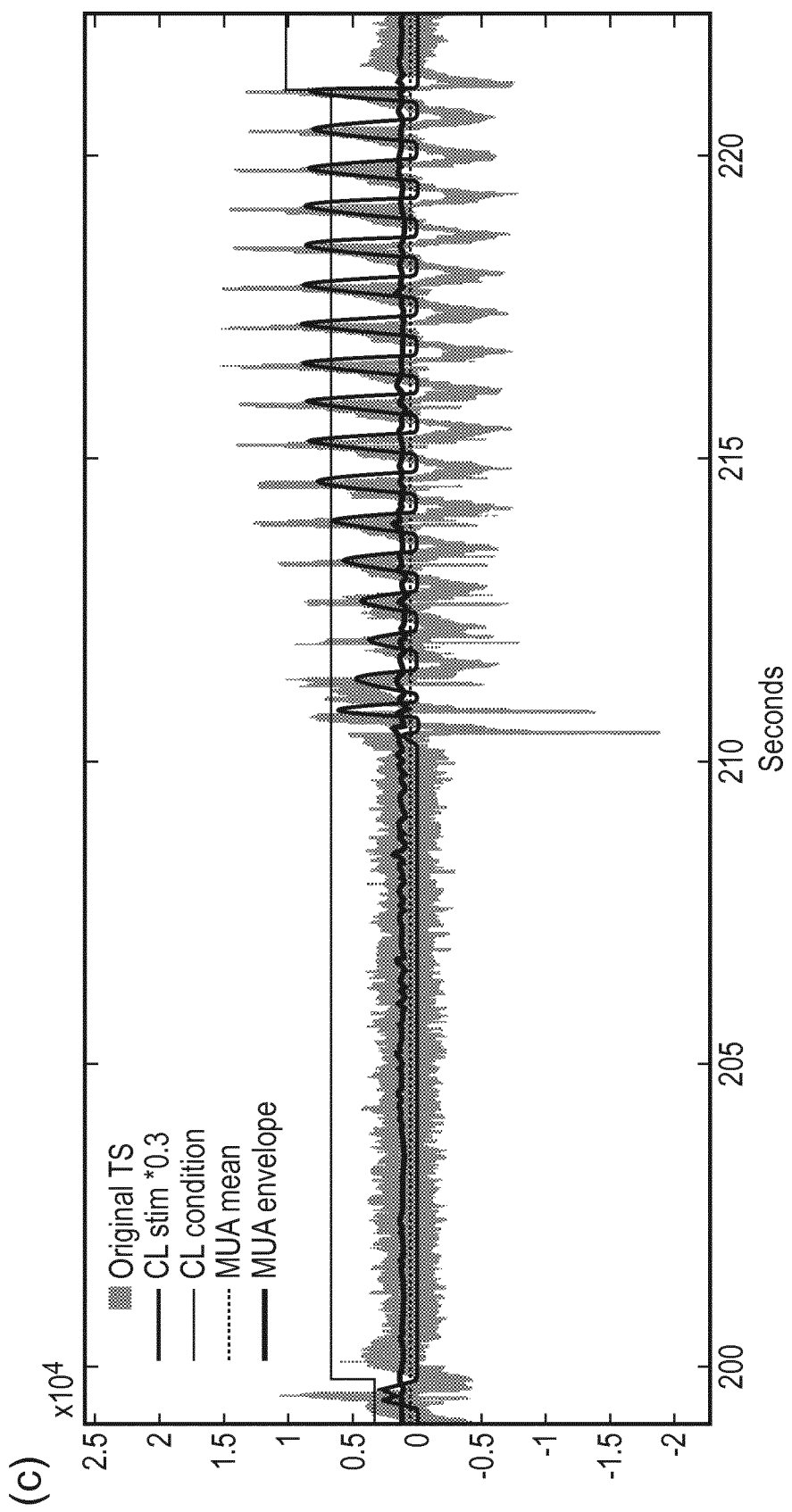

The closed-loop stimulation, in vitro, is able to stabilise a single interictal spike into a continuous low frequency oscillations, depending on the phase setting of the stimulation. FIG. 18 (taken from an example test) shows an example of this. In several cycles of running through 8 phase conditions (0, 45, 90, 135, 180, 225, 270, and 315 degrees), the behaviour is seen to be qualitatively very robust. In phases, where a stable oscillation is found, the period of the oscillation is also determined by the phase (seen in the spectrogram in FIG. 18 (b)). In some phases, no stable oscillations can be found.

Figure 19:
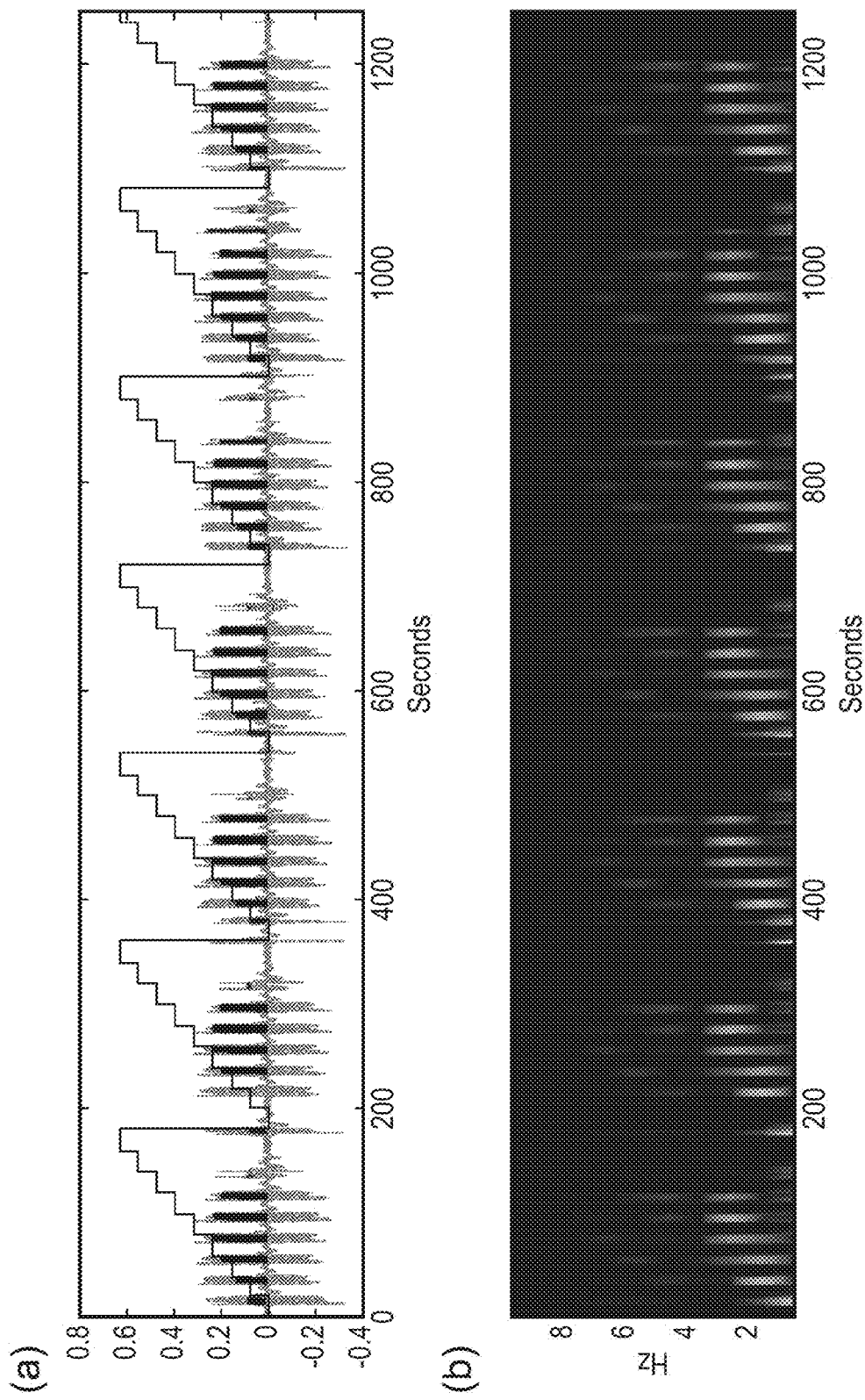
FIG. 19 shows plots from an example closed-loop stimulation on interictal spikes in silico—(a) Several cycles of simulated closed-loop stimulation with 8 phase conditions (0:45:315 degrees) shown in yellow. Blue is the simulated LFP time series, red shows the simulated LED output signal. Every setting is as in FIG. 20. (b) Spectrogram of the simulated LFP time series in (a). (c) Zoom-in of a 90 degrees phase condition from (a).
Figure 19:
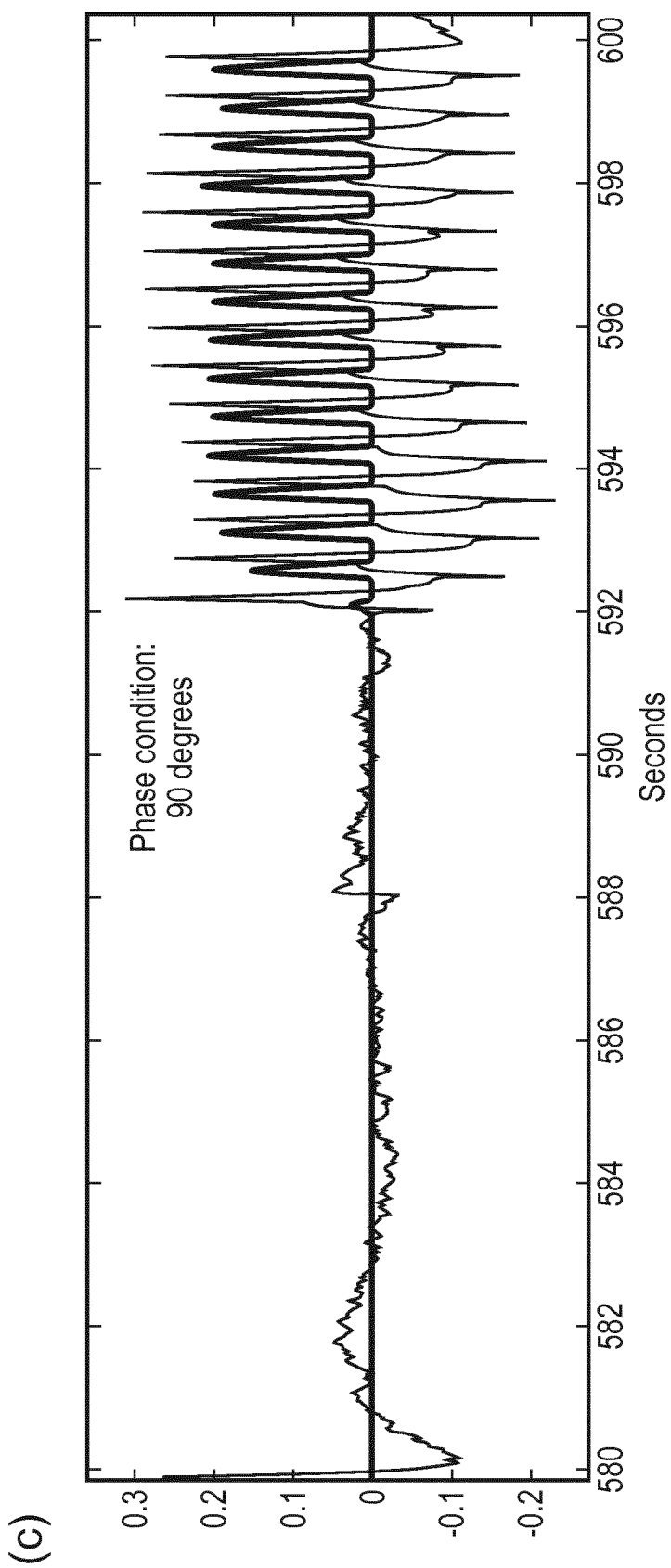

It was possible to capture most of the qualitative observations in the in silico model using the same closed-loop stimulation. FIG. 19 shows very similar observations in the simulations as in the experimental results of FIG. 18. First, depending on the phase, an oscillation is stabilised, with a few phases not being able to sustain such oscillations (FIG. 19 (a)). This behaviour is also stable across several cycles of running through the 8 phase conditions. In phases, where stable oscillations are found, the frequency is also dependent on the phase (FIG. 19 (b)). Note that the phases in which stable oscillations are found in the model depends essentially on how the simulated LFP signal is defined (in what linear combination of E(t) and I(t) it is calculated as).

The interpretation for these results is fairly simple from a dynamical systems perspective. The fact that such a simple model can capture most experimental observations indicates that the interictal spikes can be understood as an excitable system (near a simple homo-clinic bifurcation). When excited, the system completes one cycle of oscillation.

When using closed-loop stimulation, this oscillation can be stabilised. In dynamical systems terms, we can understand the stimulation as a third coupled variable, and the different phase condition can be understood as the delay of this third variable. In such a framework, it is easy to see that some phases will lead to the stabilisation of the oscillation (i.e. pushing the system beyond the bifurcation point), whereas other phases stabilise the fixed point.

Ictal Burst Activity

Figure 20:
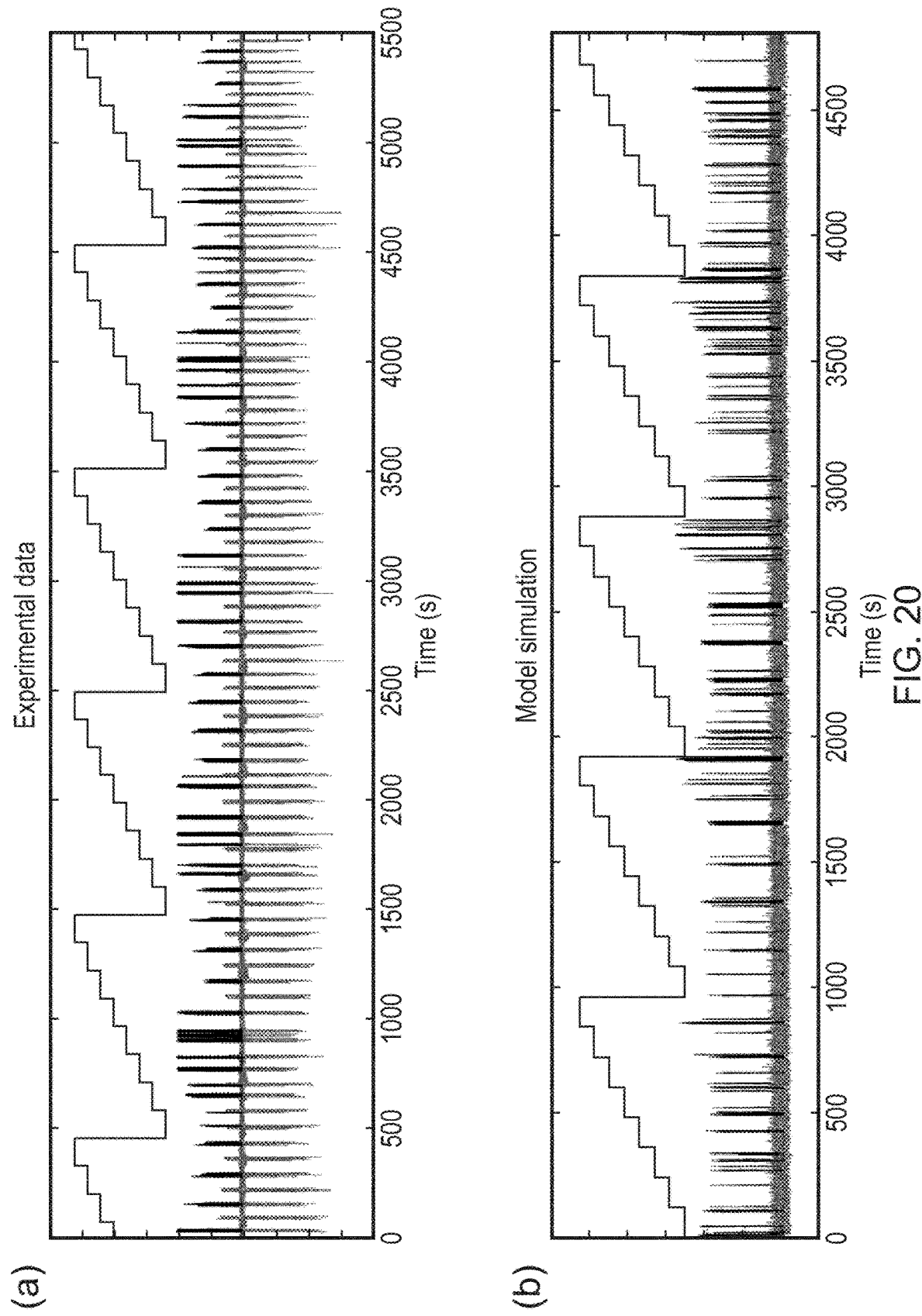
FIG. 20 shows plots from an example closed-loop stimulation on ictal discharges in vitro and in silico. (a, b) Overview of the experiment. 5 complete cycles of 8 phase conditions (shown in yellow) were tested. Blue shows the raw LFP recording, and orange shows the LED light output. (c, d) Example ictal discharges from (a/b) colour coded by phase condition.
Figure 20:
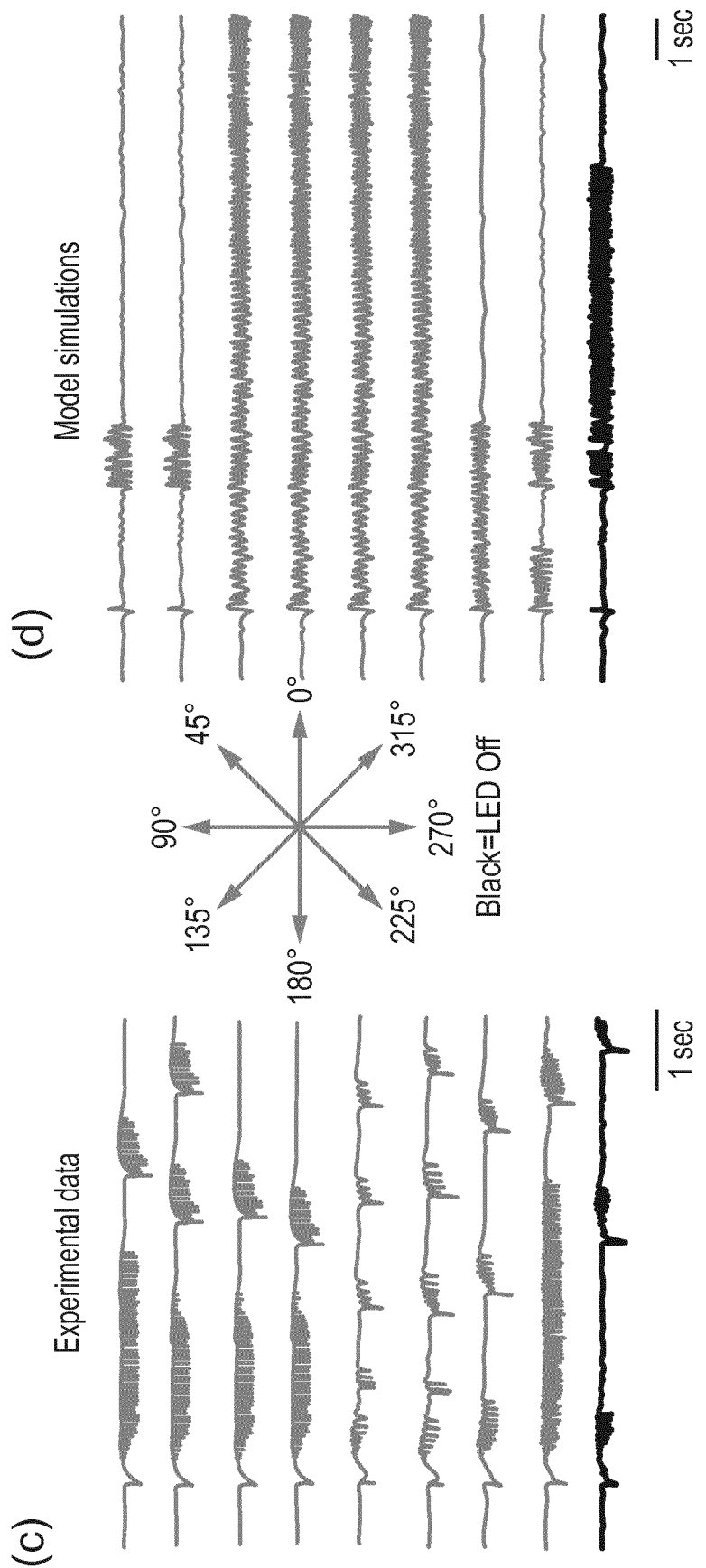

The in vitro model displays ictal burst activity, which consists of consecutive periods of beta-range high amplitude oscillatory activity, separated by background activity. During closed-loop stimulation of ictal burst activity in vitro, the essential finding was that the duration of the periods of oscillatory activity is modulated by the phase condition (FIG. 20 (c)). Some phase conditions (90 and 135 degrees) appear to shorten the duration, whereas other phase conditions appear to prolong the burst duration. However, the overall discharge duration was not changed through the stimulation. The shortening of such periods of oscillation is remarkable, given that we used EMX-ChR, i.e. probably activating principal neurons.

The in silico model at the moment is only capturing the periods of beta-range oscillations as separate events. I.e. the periodic bursting is not captured. However, it is possible to test in the simple model the effect of closed-loop stimulation. In the model the phase condition also shows an effect on the duration of the oscillatory events. In certain phase conditions, the event is prolonged by the stimulation. A slight shortening of the oscillations can also be observed at phase 0 (FIG. 20 (d)).

Figure 21:
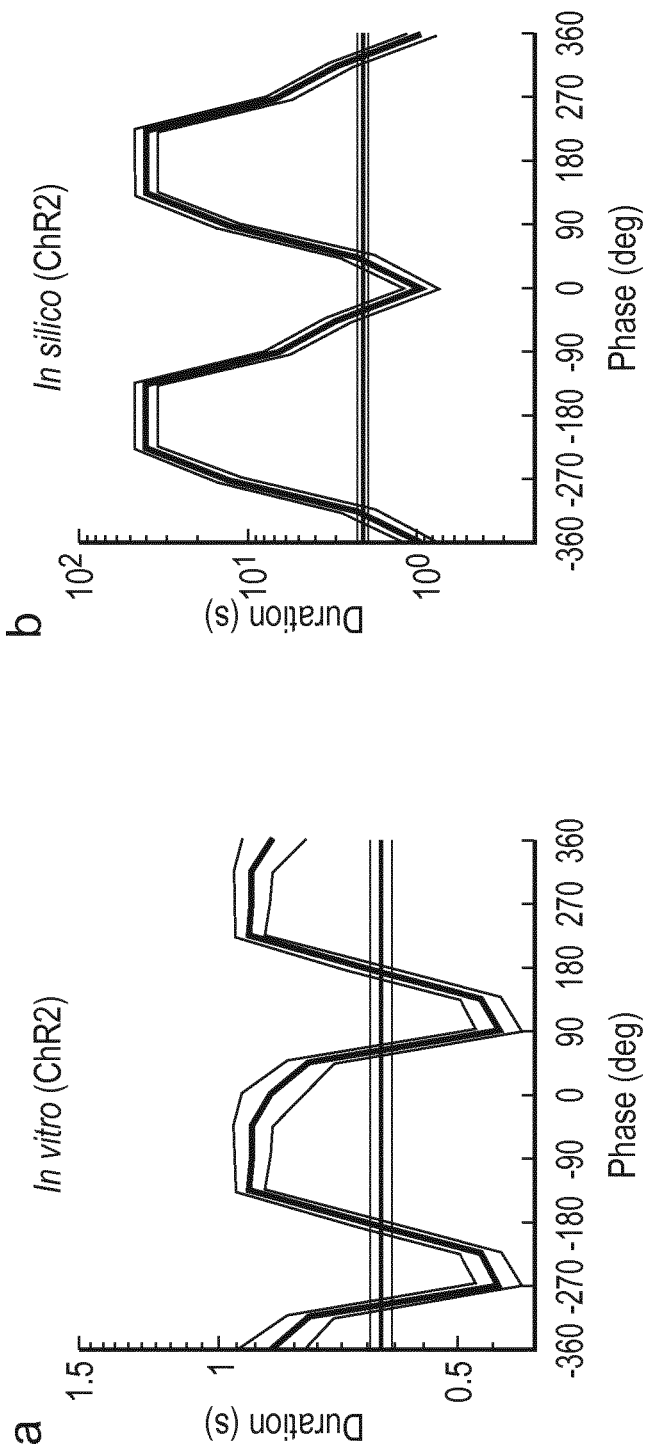
FIG. 21 shows discharge duration in different phases of closed-loop stimulation compared to the unstimulated condition. Mean and standard deviation of discharge duration is shown for each phase condition (blue). The unstimulated condition is shown in grey. (a) In vitro durations. (b) In silico durations.

To quantify this, the mean ictal burst duration is shown for each phase condition in FIG. 21. Significant changes (prolongation and shortening of bursts) are observed compared to the control condition, although the effect in the model is less prominent than the in vitro experiments. This may be due to the parameter setting of the model, which has not yet been optimized to reproduce the experiment quantitatively. Note again that the exact phase conditions for prolonging or shortening the burst duration in the model depend on the choice of how the LFP is modelled (what linear combinations of E(t) and I(t)), and the feedback strength. In this case, these parameters have not changed from the previous interictal model.

A possible interpretation of these results is that a simple bistable model of seizure activity is able to capture the prolongation, and shortening of oscillatory activity. In a similar analogy to the interictal case, the prolongation of the oscillation is fairly intuitive.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. An optogenetic system for preventing or halting seizures by stabilizing brain regions, the system including:
   a sensor for monitoring an activity of a neural network containing a group of target neurons, and generating an input signal indicative of said activity, the group of target neurons being exclusively excitatory neurons which express optogenetic actuators that cause the cells on which they are expressed to execute excitatory behavior in response to an optical stimulus;
   an optical stimulator for delivering an excitatory stimulus in the form of an optical signal to the group of target neurons, the optical signal determined based on the input signal, to reduce the overall activity of the group of target neurons; and
   a processor configured to generate an output signal based on the input signal, wherein the output signal is used to generate the optical signal which forms the excitatory stimulus, wherein: the input signal is oscillatory in nature, and the output signal has the same frequency as the input signal, and wherein the output signal is phase shifted relative to the input signal to provide a phase-shifted optical signal, and the processor is configured to determine or calculate the phase shift,
   wherein the phase shift is predetermined and fixed, and wherein the processor is configured to calculate the phase shift of the output signal based on the input signal, wherein the processor is configured to identify a range of phases during the oscillation of the input signal at which the delivery of the excitatory stimulus causes a brain region to approach a stable state, and to calculate the phase shift of the output signal based on this identification.

2. The optogenetic system of claim 1, wherein the sensor is located on an implantable device.

3. The optogenetic system of claim 2, wherein the sensor includes an electrode.

4. The optogenetic system of claim 3, wherein the sensor includes an array of electrodes.

5. The optogenetic system of claim 3, wherein the electrode is configured to monitor a local field potential of the neural network containing the target group of neurons.

6. The optogenetic system of claim 1, wherein the optical stimulator is located on an implantable device.

7. The optogenetic system of claim 6, wherein the optical stimulator and the sensor are located on the same implantable device.

8. The optogenetic system of claim 1, wherein the optical stimulator includes a light-emitting element configured to provide light having a light intensity of no less than 0.5 mW/mm$^2$, and wherein the light emitting element comprises a light emitting diode or a laser.

9. The optogenetic system of claim 8, wherein the optical stimulator includes an array of light-emitting elements.

10. The optogenetic system of claim 1, wherein the input signal is an electrical signal.

11. The optogenetic system of claim 1, wherein the output signal is an electrical signal.

12. The optogenetic system of claim 1, wherein, either:
   (a) the processor is configured to detect, within the input signal, an event signal which is indicative of an onset or presence of a seizure or seizure-like event, or
   (b) the sensor is configured to detect an event signal which is indicative of the onset or presence of a seizure or seizure-like event, and to send the input signal, and information relating to the event signal to the processor.

13. The optogenetic system of claim 1, wherein the optical stimulator is configured only to deliver the excitatory stimulus in response to a detection of an event signal.

14. The optogenetic system of claim 13, wherein the processor is configured to generate the output signal only upon the detection of the event signal.

15. The optogenetic system of claim 1, wherein the phase shift is no less than 60° and no more than 165°.

16. The optogenetic system of claim 1, wherein the phase shift is either:
   (a) no less than −30° and no more than 30°, or
   (b) no less than 150° and no more than 210°.

17. The optogenetic system of claim 1, wherein the processor is configured to perform band-pass filtering on the input signal, the band-pass filtering having a predetermined filter frequency.

18. The optogenetic system of claim 17, wherein the filter frequency is no less than 1 Hz and no more than 20 Hz.

19. The optogenetic system of claim 1, wherein the processor is configured to perform thresholding and rectification on the input signal, such that an amplitude of the output signal is proportional to an extent to which the input signal exceeds a predetermined threshold.

20. The optogenetic system of claim 1, wherein the output signal is used to control an intensity of the light emitted by the optical stimulator to generate the optical signal which forms the excitatory stimulus.

21. The optogenetic system of claim 1, wherein the output signal is used to modulate a width or frequency of pulses of light, having a constant intensity, to generate the optical signal which forms the excitatory stimulus.

22. A method of halting or preventing seizures by stabilizing brain regions, the method involving the steps of:
   monitoring an activity of a neural network containing a group of target neurons, the group of target neurons being exclusively excitatory neurons which express optogenetic actuators that cause the cells on which they are expressed to execute excitatory behavior in response to an optical stimulus;
   generating an oscillatory input signal indicative of the activity;
   generating an output signal using a processor based on the input signal, wherein the output signal has the same frequency as the input signal, wherein the output signal is phase shifted relative to the input signal to provide a phase-shifted optical signal, and wherein the processor is configured to determine or calculate the phase shift;
   determining, based on the input-signal, an optical signal for stimulating the group of target neurons, such that when delivered to the group of target neurons, the overall activity of the group of target neurons is reduced; and
   delivering an excitatory stimulus to the group of target neurons in the form of the optical signal,
   wherein the phase shift is predetermined and fixed, and wherein the processor is configured to calculate the phase shift of the output signal based on the input signal, wherein the processor is configured to identify a range of phases during the oscillation of the input signal at which the delivery of the excitatory stimulus causes a brain region to approach a stable state, and to calculate the phase shift of the output signal based on this identification.

23. The optogenetic system of claim 1, wherein the group of target neurons are genetically modified to express the optogenetic actuators using a promoter, the promoter being present in excitatory neurons and not present in inhibitory neurons.

24. The optogenetic system of claim 23, wherein the promoter is an EMX promoter.

25. The optogenetic system of claim 24, wherein the promoter is an EMX1 promoter.

26. The optogenetic system of claim 24, wherein the modified gene product is EMX1.

27. The optogenetic system of claim 1, wherein the optogenetic actuators are opsins.

28. The optogenetic system of claim 27, wherein the opsins are Channelrhodopsin 2 (ChR2), Chronos, Chrimson, or ReaChR.

\* \* \* \* \*